United States Patent
Krainer et al.

(10) Patent No.: US 10,647,983 B2
(45) Date of Patent: May 12, 2020

(54) REDUCING NONSENSE-MEDIATED MRNA DECAY

(71) Applicant: Cold Spring Harbor Laboratory, Cold Spring Harbor, NY (US)

(72) Inventors: Adrian Krainer, Huntington Station, NY (US); Isabel Aznarez, Queens, NY (US); Tomoki Nomakuchi, Syosset, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 14/916,561

(22) PCT Filed: Sep. 4, 2014

(86) PCT No.: PCT/US2014/054151
§ 371 (c)(1),
(2) Date: Mar. 3, 2016

(87) PCT Pub. No.: WO2015/035091
PCT Pub. Date: Mar. 12, 2015

(65) Prior Publication Data
US 2016/0194630 A1 Jul. 7, 2016
US 2017/0159049 A9 Jun. 8, 2017

Related U.S. Application Data

(60) Provisional application No. 61/873,780, filed on Sep. 4, 2013.

(51) Int. Cl.
| | | |
|---|---|---|
| *C12N 15/11* | (2006.01) | |
| *A61K 31/713* | (2006.01) | |
| *C12Q 1/6883* | (2018.01) | |
| *A61K 31/4245* | (2006.01) | |
| *A61K 31/726* | (2006.01) | |
| *C07H 21/02* | (2006.01) | |

(52) U.S. Cl.
CPC ........ *C12N 15/111* (2013.01); *A61K 31/4245* (2013.01); *A61K 31/713* (2013.01); *A61K 31/726* (2013.01); *C12Q 1/6883* (2013.01); *C12N 2310/11* (2013.01); *C12N 2320/30* (2013.01); *C12N 2320/31* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2005/0233327 A1   10/2005   Welch et al.

FOREIGN PATENT DOCUMENTS

WO   WO 2011/005566 A2   1/2011

OTHER PUBLICATIONS

International Preliminary Report on Patentability for Application No. PCT/US2014/054151 dated Mar. 17, 2016.
Extended European Search Report for Application No. EP 14842672.9 dated Mar. 29, 2017.
Nomakuchi et al., Antisense oligonucleotide-directed inhibition of nonsense-mediated mRNA decay. Nat Biotechnol. Feb. 2016;34(2):164-6. doi: 10.1038/nbt.3427. Epub Dec. 14, 2015.
Rodríguez-Pascau et al., Antisense oligonucleotide treatment for a pseudoexon-generating mutation in the NPC1 gene causing Niemann-Pick type C disease. Hum Mutat. Nov. 2009;30(11):E993-E1001. doi: 10.1002/humu.21119.
International Search Report and Written Opinion for International Application No. PCT/US2014/054151 dated Dec. 2, 2014.
Bhuvanagiri et al., NMD: RNA biology meets human genetic medicine. Biochem J. Sep. 15, 2010;430(3):365-77. doi: 10.1042/BJ20100699. Review.
Gong et al., Inhibition of nonsense-mediated mRNA decay by antisense morpholino oligonucleotides restores functional expression of hERG nonsense and frameshift mutations in long-QT syndrome. J Mol Cell Cardiol. Jan. 2011;50(1):223-9. doi: 10.1016/j.yjmcc.2010.10.022. Epub Oct. 28, 2010.
Kuzmiak et al., Applying nonsense-mediated mRNA decay research to the clinic: progress and challenges. Trends Mol Med. Jul. 2006;12(7):306-16. Epub Jun. 16, 2006. Review.
Vecsler et al., Ex vivo treatment with a novel synthetic aminoglycoside NB54 in primary fibroblasts from Rett syndrome patients suppresses MECP2 nonsense mutations. PLoS One. 2011;6(6):e20733. doi: 10.1371/journal.pone.0020733. Epub Jun. 13, 2011.
PCT/US2014/054151, Mar. 17, 2016, International Preliminary Report on Patentability.
EP 14842672.9, Mar. 29, 2017, Extended European Search Report.
PCT/US2014/054151, Dec. 2, 2014, International Search Report and Written Opinion.

*Primary Examiner* — Sean McGarry
(74) *Attorney, Agent, or Firm* — Wolf, Greenfield & Sacks, P.C.

(57) ABSTRACT

The present disclosure relates to compositions and methods for inhibiting nonsense-mediated mRNA decay in a gene-specific manner, for example in the treatment of diseases or disorders caused by nonsense mutations.

15 Claims, 6 Drawing Sheets
Specification includes a Sequence Listing.

A

| % Wild Type | | T39 treated with ASO |||||||||||||||||||
|---|---|---|---|---|---|---|---|---|---|---|---|---|---|---|---|---|---|---|---|
| | WT | No ASO | 234 | 235 | 236 | 237 | 238 | 239 | 240 | 241 | 242 | 243 | 244 | 245 | 246 | 247 | 248 | 249 | 250 | 251 |
| | 100 | 60 | 48 | 28 | 28 | 22 | 10 | 2 | 1 | 1 | 3 | 6 | 50 | 52 | 73 | 91 | 68 | 48 | 57 | 64 |

B p=0.005

C

| Fold Change HBB-T39 | No ASO | ASO-247 |
|---|---|---|
| | 1.0 | 6.0 |

| Fold Change | | | | | | | +ASO-479 (50nM+50nM) | | | | | |
|---|---|---|---|---|---|---|---|---|---|---|---|---|
| | 492 | 493 | 501 | 502 | 503 | 504 | 492 | 492 | 501 | 502 | 503 | 504 |
| | 2.0 | 2.0 | 0.8 | 1.4 | 1.4 | 2.0 | 1.4 | 1.4 | 1.0 | 1.8 | 1.6 | 1.9 |

↓Individual ASOs used to target respective downstream EJC (dEJC)

REDUCING NONSENSE-MEDIATED MRNA DECAY

RELATED APPLICATIONS

This application is a national stage filing under 35 U.S.C. § 371 of international application number PCT/US2014/054151, filed Sep. 4, 2014, which was published under PCT Article 21(2) in English and claims the benefit under 35 U.S.C. § 119(e) of U.S. provisional application Ser. No. 61/873,780, filed Sep. 4, 2013, each of which is herein incorporated by reference in its entirety.

FEDERALLY SPONSORED RESEARCH

This invention was made with government support under Grant number R21 NS081448-01 awarded by National Institutes of Health/National Institute of Neurological Disorders and Stroke (NIH/NINDS). The government has certain rights in the invention.

BACKGROUND

The causal mutation in many genetic diseases is a nonsense mutation. Additional approaches to treating or preventing diseases in which nonsense mutations play a role are needed.

SUMMARY

As described herein, antisense oligonucleotides (ASOs) are able to inhibit exon junction complex (EJC) deposition, and, in the context of transcripts containing nonsense mutations, inhibit nonsense mediated mRNA decay (NMD) of the transcripts. Provided herein are methods of inhibiting NMD in a gene-specific manner, such as in treatment of a disease or disorder caused by a nonsense mutation, or reduction of the extent to which a disease or disorder occurs, and compositions useful for inhibiting NMD in a gene-specific manner, including in the methods described herein.

The methods and compositions described herein are capable of inhibiting NMD in a gene-specific manner by specifically targeting a gene that is associated with a disease or a gene that contains a disease-causing mutation (e.g., a nonsense mutation). In some embodiments, the disease-causing mutation results in a premature termination codon (PTC). In some embodiments, the gene contains a PTC that is naturally occurring, e.g. the PTC is not the result of a mutation. In some embodiments, the PTC results NMD of the transcript, and reduced quantities of the polypeptide encoded by the gene. The ASOs provided herein, specifically bind to a nucleic acid in a target mRNA and inhibit NMD resulting in increased production of the polypeptide, or truncated polypeptide, encoded by the gene.

One embodiment is a method of inhibiting nonsense-mediated decay (NMD) of mRNA in a gene-specific manner in a eukaryotic cell. The method involves contacting (a) a eukaryotic cell that comprises (i) a nucleic acid that contains a disease-causing premature termination codon (PTC) or a naturally-occurring premature termination codon (PTC) and (ii) mRNA encoded by the nucleic acid with (b) an antisense oligonucleotide (ASO) specific to and sufficiently complementary to a region of the mRNA that is from about 1 to about 50 nucleotides upstream of an exon-exon junction that (i) is located downstream from the PTC and (ii) when marked by deposition of exon junction complexes (EJC), marks the mRNA for nonsense-mediated decay, under conditions under which the ASO enters the cell in sufficient quantity to inhibit deposition of EJC at the exon-exon junction and inhibit NMD of the mRNA that contains the PTC. In some embodiments, the ASO enters the nucleus of the cell in sufficient quantity to inhibit deposition of EJC at the exon-exon junction and inhibit NMD of the mRNA that contains the PTC. In some embodiments, the disease-causing PTC results from a mutation. In some embodiments, the ASO is specific to a region of the nucleic acid that is from about 20 to about 24 nucleotides upstream of an exon-exon junction. In some embodiments, the ASO is no less than 14 nucleotides in length (at least 14 nucleotides in length). In some embodiments, the nucleic acid is a HBB allele that contains a nonsense mutation (e.g., for example, the HBB allele can be CM810001, CM880039, CM034660, CM880040, or CM900122). In some embodiments, the ASO is selected from SEQ ID NOs: 1-19. In some embodiments, the ASO is SEQ ID NO:15 or SEQ ID NO:16. In other embodiments, the nucleic acid is an MECP2 allele that contains a nonsense mutation (e.g., the MECP2 allele is CM060329, CM023409, HM971529, CM010332, CM057720, CM010333, CM035705, CM055984, or CM076290). In some embodiments, the ASO is selected from SEQ ID NOs:20-38. In some embodiments, the ASO is selected from SEQ ID NO:29, SEQ ID NO:30, SEQ ID NO:31, or SEQ ID NO:32. In some embodiments, the eukaryotic cell is in an individual, such as in a human.

Another embodiment is a method of inhibiting deposition of exon junction complexes (EJC) in a gene-specific manner in a eukaryotic cell. The method-comprises introducing, into a eukaryotic cell that comprises an exon-exon junction that is (i) downstream of a disease-causing premature termination codon or a naturally-occurring premature termination codon (PTC) in mRNA transcribed in the eukaryotic cell and (ii) bound by an exon junction complex (EJC) that identifies (marks) the mRNA for nonsense-mediated decay (NMD), an antisense oligonucleotide (ASO) specific to the mRNA from about 1 to about 50 nucleotides upstream of the exon-exon junction, in sufficient quantity and under conditions under which the ASO blocks binding or deposition of EJC to the exon-exon junction. In one embodiment, the method involves (a) identifying (determining the location of) an exon-exon junction that is (i) downstream of a disease-causing premature termination codon or a naturally-occurring premature termination codon (PTC) in mRNA transcribed in the eukaryotic cell and (ii) bound by an exon junction complex (EJC) that identifies (marks) the mRNA for nonsense-mediated decay (NMD); and (b) introducing into the cell an antisense oligonucleotide (ASO) specific to the mRNA from about 1 to about 50 nucleotides upstream of the exon-exon junction identified in (a) in sufficient quantity and under conditions under which the ASO blocks binding or deposition of EJC to the exon-exon junction. In some embodiments, the disease-causing PTC results from a mutation. In some embodiments, the ASO is specific to a region of the nucleic acid that is from about 20 to about 24 nucleotides upstream of an exon-exon junction. In some embodiments, the ASO is no less than 14 nucleotides in length (at least 14 nucleotides in length). In some embodiments, the ASO is 18 nucleotides in length. In some embodiments, the mRNA is transcribed from a HBB allele that contains a nonsense mutation, such as CM810001, CM880039, CM034660, CM880040, or CM900122. In some embodiments, the ASO is selected from SEQ ID NOs: 1-19. In some embodiments, the ASO is SEQ ID NO:15 or SEQ ID NO:16. In some embodiments, the mRNA is transcribed from a MECP2 allele that contains a nonsense mutation, such as CM060329, CM023409, HM971529, CM010332, CM057720, CM010333, CM035705, CM055984, or CM076290. In some embodiments, the ASO is selected from SEQ ID NOs:20-38. In some embodiments, the ASO is selected from SEQ ID NO:29, SEQ ID NO:30, SEQ ID NO:31, or SEQ ID NO:32. In some embodiments, the eukaryotic cell is in an individual, for example, a human.

Another embodiment is a method of increasing the amount of a truncated protein encoded by a gene that contains a premature termination codon (PTC) produced in a eukaryotic cell. The method involves (a) identifying (determining the location of) an exon-exon junction that is downstream of a disease-causing premature termination codon or a naturally occurring premature termination codon (PTC) in mRNA transcribed in the eukaryotic cell; and (b) introducing into the eukaryotic cell an antisense oligonucleotide (ASO) specific to a region of the mRNA that is from about 1 to about 50 nucleotides upstream of an exon-exon junction identified in (a), to which deposition of exon junction complexes (EJC) marks the mRNA for nonsense-mediated decay, under conditions under which the ASO enters the cell in sufficient quantity to inhibit deposition of an EJC upstream of the exon-exon junction that is located downstream of the PTC and inhibits NMD of mRNA that contains the PTC and protein production occurs. In some embodiments, the disease-causing PTC results from a mutation. In some embodiments, the ASO is specific to a region of the nucleic acid that is from about 20 to about 24 nucleotides upstream of an exon-exon junction. In some embodiments, the ASO is no less than 14 nucleotides in length (is at least 14 nucleotides). In some embodiments, the method further comprises administering a compound that promotes the readthrough of PTCs. In some embodiments, the compound that promotes the readthrough of PTCs is ataluren or an aminoglycoside. In some embodiments, the aminoglycoside is amikacin, arbekacin, gentamicin, kanamycin, neomycin, netilmicin, paromomycin, rhodostreptomycin, streptomycin, tobramycin, apramycin, G418 (geneticin), lividomycin, or an aminoglycoside analog chosen from NB30, NB54, or NB84. In some embodiments, the eukaryotic cell is in an individual, for example, a human.

A further embodiment is a method of increasing the efficacy of a readthrough drug in a eukaryotic cell. The method comprises:
  (a) identifying (determining the location/sequence of) an exon-exon junction that is downstream of a disease-causing or naturally occurring premature termination codon (PTC) in mRNA transcribed in a eukaryotic cell;
  (b) introducing into the eukaryotic cell an antisense oligonucleotide (ASO) specific to a region of the mRNA that is from about 1 to about 50 nucleotides upstream of the exon-exon junction identified in (a), to which deposition of exon junction complexes (EJC) marks the mRNA for nonsense-mediated decay, under conditions under which (i) the ASO enters the cell in sufficient quantity to inhibit deposition of EJC at the exon-exon junction and inhibits NMD of mRNA that contains the PTC and (ii) protein production occurs; and
  (c) introducing into the eukaryotic cell a composition that promotes readthrough of PTC (a readthrough drug) in sufficient quantity (and under conditions under which the composition enters the cell) to result in larger amounts of full-length protein translated from the mRNA that contains the PTC than would occur in the absence of ASO introduced in (b).

In some embodiments, the disease-causing PTC results from a mutation. In some embodiments, the ASO is specific to a region of the nucleic acid that is from about 20 to about 24 nucleotides upstream of an exon-exon junction. In some embodiments, the ASO is no less than 14 nucleotides in length (at least 14 nucleotides in length). In some embodiments, the mRNA is transcribed from a HBB allele that contains a nonsense mutation, such as CM810001, CM880039, CM034660, CM880040, or CM900122. In some embodiments, the ASO is selected from SEQ ID NOs: 1-19. In some embodiments, the ASO is SEQ ID NO:15 or SEQ ID NO:16. In some embodiments, the mRNA is transcribed from a MECP2 allele that contains a nonsense mutation, such as CM060329, CM023409, HM971529, CM010332, CM057720, CM010333, CM035705, CM055984, or CM076290. In some embodiments, the ASO is selected from SEQ ID NOs:20-38. In some embodiments, the ASO is selected from SEQ ID NO:29, SEQ ID NO:30, SEQ ID NO:31, or SEQ ID NO:32. In some embodiments, the composition that promotes the readthrough of PTCs is ataluren or an aminoglycoside. In some embodiments, the aminoglycoside is amikacin, arbekacin, gentamicin, kanamycin, neomycin, netilmicin, paromomycin, rhodostreptomycin, streptomycin, tobramycin, apramycin, G418 (geneticin), lividomycin, or an aminoglycoside analog chosen from NB30, NB54, or NB84. In some embodiments, the eukaryotic cell is in an individual, such as a human.

Also described is a method of treating an individual having or at an increased risk of having a disease caused by a mutation that introduces a premature termination codon (PTC) in an mRNA. The method comprises administering to the individual a pharmaceutical composition comprising a therapeutically effective amount of an ASO that inhibits NMD of the PTC-containing mRNA. In some embodiments, the disease is β-thalassemia. For example, the β-thalassemia is caused by an HBB allele that contains a nonsense mutation selected from CM810001, CM880039, CM034660, CM880040, and CM900122. In some aspects, the ASO, for example in treating β-thalassemia, is selected from SEQ ID NOs: 1-19. In some embodiments, the ASO for treating β-thalassemia is SEQ ID NO:15 or SEQ ID NO:16. In some embodiments, the disease to be treated is Rett syndrome. For example, the Rett syndrome is caused by a MECP2 allele that contains a nonsense mutation selected from CM060329, CM023409, HM971529, CM010332, CM057720, CM010333, CM035705, CM055984, and CM076290. In some embodiments, the ASO, for example in treating Rett syndrome, is selected from SEQ ID NOs:20-38. In some embodiments, the ASO for treating Rett syndrome is selected from SEQ ID NO:29, SEQ ID NO:30, SEQ ID NO:31, and SEQ ID NO:32. In some embodiments, the method of treating an individual further comprises administering a therapeutically effective amount of a compound that promotes the readthrough of PTCs. For example, the compound is ataluren or an aminoglycoside. In some embodiments, the aminoglycoside is amikacin, arbekacin, gentamicin, kanamycin, neomycin, netilmicin, paromomycin, rhodostreptomycin, streptomycin, tobramycin, apramycin, G418 (geneticin), lividomycin, or an aminoglycoside analog chosen from NB30, NB54, or NB84.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

DETAILED DESCRIPTION

Figure 1:
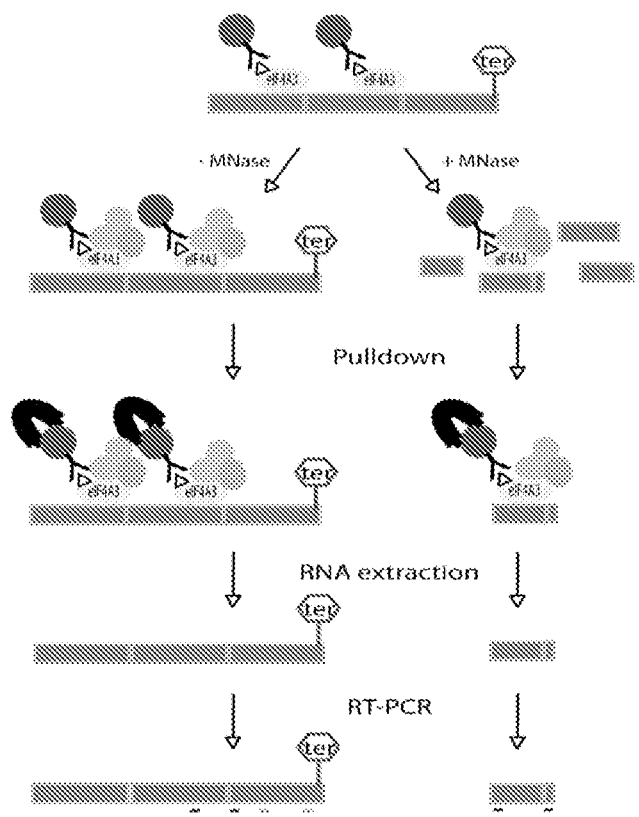
FIG. 1 is a schematic representation of a RNA immunoprecipitation (RIP), MNase treatment, and RT-PCR protocol for identifying EJC-bound exon-exon junctions. Triangle denotes the T7 tag. Blue and brown horizontal bars denote primers that amplify a 60-nt region spanning the exon-exon junction and "control region", respectively.

Nonsense mutations introduce premature termination codons (PTCs) in transcripts, resulting in truncated proteins, and often severe disease presentations. Transcripts containing PTCs are typically degraded by nonsense mediated mRNA decay (NMD), which often further impacts such diseases.

Approximately one third of alleles causing genetic diseases carry nonsense mutations that introduce PTCs (6). In recent years, efforts have been made to develop translational readthrough therapies for treatment of diseases caused by nonsense mutations. One promising drug, ataluren, now known as Translarna (formerly known as PTC124), currently in Phase III clinical trials for cystic fibrosis and approved conditionally in European Medicines Agent (EMA) for Duchenne muscular dystrophy, was developed by PTC Therapeutics (South Plainfield, N.J.). Ataluren presumably binds to the ribosomal A site, causing conformational changes that allow mispairing between the mRNA codon and tRNA anticodon, which results in incorporation of an amino acid at a PTC (6). This readthrough occurs minimally at normal stop codons, because additional surrounding sequences, as well as the proximity to the poly A tail, ensure efficient stop-codon recognition (6).

The efficiency of readthrough of PTCs by ataluren and other agents is relatively low, but it is beneficial in diseases in which even low levels of full-length protein are sufficient to improve cell function (completely or partially). The outcome of this treatment is highly variable among patients. At the gene level, the variability can be due in part to the identity and sequence context of the PTC (e.g., UGA>UAG>UAA) (6). However, this cannot explain the variability observed in response to readthrough agents among patients participating in the same study who carry the same mutation (5, 6). These observations led to the suspicion that variability in a quality-control mechanism termed nonsense-mediated mRNA decay (NMD) could influence the outcome of the treatment. The NMD pathway is a quality-control step during gene expression that is relevant to genetic diseases because it degrades PTC-containing transcripts to prevent the synthesis of truncated, potentially deleterious proteins. Generally, transcripts containing PTCs located more than 50-55 nucleotides upstream of the last exon-exon junction elicit NMD (4). Pre-mRNA splicing is a prerequisite for NMD. This is the case because, concomitantly or immediately after two exons are spliced together, a complex of proteins termed the exon junction complex (EJC) is deposited upstream (e.g., from about 20 to about 24 nucleotides) of each exon-exon junction (11). The EJC consists of four core components, the anchor eIF4A3, Y14, Magoh and MLN51 proteins, and associated proteins that are involved in mRNA export (11). The core tetramer facilitates the recruitment of the first two NMD factors, UPF3B and UPF2. Subsequently, during a pioneer round of translation, when a ribosome encounters a stop codon upstream of an EJC, the third and key NMD factor, UPF1, is recruited to the transcript through interaction with UPF2, marking the transcript for degradation (13). Thus, it is presumed that the presence of a downstream EJC distinguishes a PTC from a normal stop codon, thereby signaling (marking it) for NMD.

The efficiency with which NMD degrades PTC-containing transcripts is variable. This variability has been observed not only for different mutations, but also for the same mutation in different cell types, or among patients (5, 6, 14). The efficiency of NMD can have a direct effect on the response to readthrough therapies, at least in part because the availability of PTC-containing transcripts is key to the success of ataluren and other readthrough agents, such as aminoglycoside antibiotics. This was demonstrated by studies in which NMD was inhibited by either knocking down UPF1 or administering NMD1-1, a compound that attenuates NMD globally, which dramatically improved the efficiency of the readthrough drug gentamycin (5, 15). Knocking down UPF1 or attending NMD in patients is not a viable approach, however, because it would affect NMD globally and would be detrimental to patients' health. Additionally, several pharmacological agents have been identified which inhibit NMD, including cycloheximide, emetine, puromycin, and pateamine A (16). However, these drugs are not ideal candidates for therapeutic use as NMD inhibitors, they inhibit NMD globally and are generally toxic.

The work described herein relates, in part, to antisense technology useful to abrogate or inhibit NMD in a gene specific manner, thus obviating concerns relating to global NMD inhibition. As described herein, binding of antisense oligonucleotides (ASOs, e.g., uniform 2'-O-(2-methoxyethyl) (MOE) phosphorothioate-modified ASOs) to transcripts containing PTCs interferes with the deposition of EJCs at exon-exon junctions downstream of PTCs, thereby removing the landmarks that single out PTCs and inhibiting NMD in a gene-specific manner. Inhibition of NMD increases the availability of PTC-containing transcripts, which increases the efficacy of readthrough drugs because there are more PTC-containing transcript molecules on which the drugs can act. This results in the production of more full-length protein than would occur in the absence of inhibition of NMD. In addition, inhibition of NMD in a gene-specific manner is beneficial to patients with nonsense mutations that result in production of a truncated protein that retains normal or partial function (17). Promoting stabilization of the mRNA and therefore translation of a truncated protein by NMD inhibition (without co-treatment with a readthrough drug) could significantly improve the outcome of a disease.

Diseases

Any nonsense mutation occurring downstream of the first exon and at least 50-55 nucleotides upstream of the last exon-exon junction can be treated by the methodology and compositions provided herein. Mutations that follow this rule are referred to as "treatable" mutations. EJC deposition is blocked at at least one exon-exon junction and, in some embodiments, at more than one exon-exon junction downstream of a PTC, simultaneously, to provide for enhanced inhibition of NMD. The vast majority of genes in the human genome have at least two exons (the average number of exons per gene in the human genome is approximately eight), which means that nonsense mutations in many disease-associated genes are treatable mutations that can be targeted by the disclosed methodology.

In some embodiments, the compositions and methodology are useful for inhibiting NMD of transcripts derived from a disease-associated gene, such as CFTR, DMD, HBB, MECP2 and IDUA. Mutations in these genes cause, respectively, cystic fibrosis (1/2500 live births), Duchenne/Becker muscular dystrophy (1/4000 male live births), β-thalassemia (1/158-1/25,000 live births, Rett syndrome (1/10,000-15,000 female live births), and mucopolysaccharidosis type 1-Hurler (1/100,000). A subset of nonsense mutations that cause these diseases have been targeted by readthrough drugs (3, 15, 17, 20, 22). Table 1 provides examples of candidate nonsense mutations in each of the five genes (from the human gene mutation database, www.hgmd.org) that are "treatable" based on the characteristics mentioned above.

TABLE 1

List of treatable nonsense mutations for Rett syndrome (mutations in MECP2), cystic fibrosis (and in some cases congenital bilateral absence of the vas deferens (CBAVD), associated with cystic fibrosis) (mutations in CFTR), β-thalassemia (mutations in HBB), Duchenne/Becker muscular dystrophy (DMD/BMD, dystrophinopathy) (mutations in DMD), and mucopolysaccharidosis type 1-Hurler (mutation in IDUA).

| Accession number | Codon change | Am. ac. change | Codon | Disease |
|---|---|---|---|---|
| CM060329 | gGAA-TAA | Glu-Ter | 10 | Rett syndrome |
| CM023409 | cCAG-TAG | Gln-Ter | 16 | Rett syndrome |

TABLE 1-continued

List of treatable nonsense mutations for Rett syndrome (mutations in MECP2), cystic fibrosis (and in some cases congenital bilateral absence of the vas deferens (CBAVD), associated with cystic fibrosis) (mutations in CFTR), β-thalassemia (mutations in HBB), Duchenne/Becker muscular dystrophy (DMD/BMD, dystrophinopathy) (mutations in DMD), and mucopolysaccharidosis type 1-Hurler (mutation in IDUA).

| Accession number | Codon change | Am. ac. change | Codon | Disease |
|---|---|---|---|---|
| HM971529 | cCAG-TAG | Gln-Ter | 19 | Rett syndrome |
| CM010332 | cAAG-TAG | Lys-Ter | 22 | Rett syndrome |
| CM057720 | gCAG-TAG | Gln-Ter | 47 | Rett syndrome |
| CM010333 | TCA-TAA | Ser-Ter | 49 | Rett syndrome |
| CM035705 | TCA-TGA | Ser-Ter | 65 | Rett syndrome |
| CM055984 | TCA-TGA | Ser-Ter | 68 | Rett syndrome |
| CM076290 | TGG-TAG | Trp-Ter | 104 | Rett syndrome |
| CM960290 | TTA-TAA | Leu-Ter | 1254 | Cystic fibrosis |
| CM920186 | TCA-TAA | Ser-Ter | 1255 | Cystic fibrosis |
| CM993870 | TGGg-TGA | Trp-Ter | 1274 | Cystic fibrosis |
| CM970297 | aCAG-TAG | Gln-Ter | 1281 | Cystic fibrosis |
| CM900061 | TGGa-TGA | Trp-Ter | 1282 | Cystic fibrosis |
| CM003260 | aCAG-TAG | Gln-Ter | 1291 | Cystic fibrosis |
| CM993871 | TATg-TAA | Tyr-Ter | 1307 | Cystic fibrosis |
| CM972963 | tGAA-TAA | Glu-Ter | 1308 | Cystic fibrosis |
| CM920192 | TGG-TAG | Trp-Ter | 1310 | Cystic fibrosis |
| CM930137 | tCAA-TAA | Gln-Ter | 1313 | Cystic fibrosis |
| CM900062 | TGG-TAG | Trp-Ter | 1316 | Cystic fibrosis |
| CM920194 | tGAA-TAA | Glu-Ter | 1371 | Cystic fibrosis |
| CM024696 | TACc-TAA | Tyr-Ter | 1381 | Cystic fibrosis |
| CM983581 | cCAA-TAA | Gln-Ter | 1382 | Cystic fibrosis |
| CM983582 | tGAA-TAA | Glu-Ter | 1401 | Cystic fibrosis |
| CM931253 | cCAA-TAA | Gln-Ter | 1411 | CBAVD |
| CM960291 | aCAA-TAA | Gln-Ter | 1412 | Cystic fibrosis |
| CM810001 | cCAG-TAG | Gln-Ter | 39 | β-thalassemia |
| CM880039 | tGAG-TAG | Glu-Ter | 43 | β-thalassemia |
| CM034660 | tAAG-TAG | Lys-Ter | 59 | β-thalassemia |
| CM880040 | gAAG-TAG | Lys-Ter | 61 | β-thalassemia |
| CM900122 | tGAG-TAG | Glu-Ter | 90 | β-thalassemia |
| CM054661 | TTA-TAA | Leu-Ter | 3471 | BMD |
| CM960494 | cCAG-TAG | Gln-Ter | 3493 | BMD |
| CM040028 | gGAA-TAA | Glu-Ter | 3515 | BMD |
| CM084901 | aGAA-TAA | Glu-Ter | 3516 | BMD |

TABLE 1-continued

List of treatable nonsense mutations for Rett
syndrome (mutations in MECP2), cystic fibrosis
(and in some cases congenital bilateral absence
of the vas deferens (CBAVD), associated with
cystic fibrosis)(mutations in CFTR), β-thalassemia
(mutations in HBB), Duchenne/Becker muscular
dystrophy (DMD/BMD, dystrophinopathy)
(mutations in DMD), and mucopolysaccharidosis
type 1-Hurler (mutation in IDUA).

| Accession number | Codon change | Am. ac. change | Codon | Disease |
|---|---|---|---|---|
| CM043277 | tCAG-TAG | Gln-Ter | 3625 | Dystrophinopathy |
| CM950349 | tCAA-TAA | Gln-Ter | 3635 | DMD |
| CM070908 | TCG-TAG | Ser-Ter | 3637 | BMD |
| CM022961 | aGAG-TAG | Glu-Ter | 3657 | DMD |
| CM920372 | TGG-TAG | Trp-Ter | 402 | MPSI-H |

Any disease associated with a nonsense allele may be treated using the compositions and methods provided herein. Other diseases or disorders that are also treatable using the compositions and methods provided herein include, but are not limited to, Shwachman-Diamond syndrome, Usher syndrome, ataxia telangiectasia, hemophilia A and B, Hailey-Hailey disease, Ullrich disease, methylmalonic acidemia, carnitine palmitoyltransferase 1A deficiency, peroxisome biogenesis disorders, limb girdle muscular dystrophy, Schmid metaphyseal chondrodysplasia, Sandhoff disease, Marfan syndrome, anemia, epidermolysis bullosa simplex, Tay-Sachs disease, triose phosphate isomerase deficiency, Alzheimer's disease, long-QT syndrome, insulin resistance, maple syrup urine disease, hereditary fructose intolerance, X-linked severe combined immunodeficiency, inherited cancers such as those due to BRCA1 nonsense mutations, carbohydrate metabolism disorders, amino acid metabolism disorders, lipoprotein metabolism disorders, lipid metabolism disorders, lysosomal enzymes metabolism disorders, steroid metabolism disorders, purine metabolism disorders, pyrimidine metabolism disorders, metal metabolism disorders, porphyrin metabolism disorders, and heme metabolism disorders.

ASOs

One embodiment of the present disclosure is a composition comprising nucleic acids and/or nucleic acid analogs, such as polynucleotides, that inhibit nonsense-mediated mRNA decay (NMD) in a gene-specific manner. The nucleic acids or polynucleotides are typically antisense oligonucleotides (ASOs) that bind to a specific region of an mRNA transcript and interfere with the binding of one or more components of the exon junction complex (EJC). In all embodiments herein, referring to "an mRNA," or "the mRNA" means one or more (at least one) mRNA molecules. As used herein, the terms "antisense oligonucleotide," "ASO" and "antisense oligomer" are used interchangeably and refer to a polynucleotide, comprising nucleotides, that hybridizes to a target nucleic acid (e.g., mRNA) sequence by Watson-Crick base pairing or wobble base pairing (G-U). The ASO may have exact sequence complementarity to the target sequence or near complementarity (e.g., sufficient complementarity to bind the target sequence and inhibit binding of one or more EJC components). Such ASOs block or inhibit the binding or deposition of one or more EJC components to an mRNA and do so in a gene-specific manner; ASOs are designed so that they bind (hybridize) to a target nucleic acid (e.g., a mRNA transcript) and remain hybridized under physiological conditions. Typically, if they hybridize to a site other than the intended (target) nucleic acid sequence, they hybridize to a limited number of sequences that are not a target nucleic acid (to few sites other than a target nucleic acid). Design of an ASO can take into consideration the occurrence of the target nucleic acid sequence or a sufficiently similar nucleic acid sequence in other locations in the genome or cellular mRNA/transcriptome, such that the likelihood the ASO will bind other sites and cause "off-target" effects is limited.

In some embodiments, ASOs "specifically hybridize" to or are "specific" to a target nucleic acid. Typically such hybridization occurs with a $T_m$ substantially greater than 37° C., preferably at least 50° C., and typically between 60° C. to approximately 90° C. Such hybridization preferably corresponds to stringent hybridization conditions. At a given ionic strength and pH, the $T_m$ is the temperature at which 50% of a target sequence hybridizes to a complementary oligonucleotide.

Polynucleotides (e.g., oligonucleotides, ASOs, mRNA, etc.) are "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree to which one polynucleotide is complementary with another) is quantifiable in terms of the proportion (e.g., the percentage) of bases in opposing strands that are expected to form hydrogen bonds with each other, according to generally accepted base-pairing rules. The sequence of an oligomeric compound, e.g., an ASO, need not be 100% complementary to that of its target nucleic acid to hybridize. In certain embodiments, ASOs can comprise at least about 70%, at least about 80%, at least about 90%, at least about 95%, or at least about 99% sequence complementarity to a target region within the target nucleic acid sequence to which they are targeted. For example, an ASO in which 18 of 20 nucleobases of the oligomeric compound are complementary to a target region, and would therefore specifically hybridize, would represent 90 percent complementarity. In this example, the remaining noncomplementary nucleobases may be clustered together or interspersed with complementary nucleobases and need not be contiguous to each other or to complementary nucleobases. An ASO which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an ASO with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

An ASO need not hybridize to all nucleobases in a target sequence and the nucleobases to which it does hybridize may be contiguous or noncontiguous. ASOs may hybridize over one or more segments of a target nucleic acid, such that intervening or adjacent segments are not involved in the hybridization event (e.g., a loop structure or hairpin structure may be formed). In certain embodiments, an ASO hybridizes to noncontiguous nucleobases in a target nucleic acid. For example, an ASO can hybridize to nucleobases in a target nucleic acid that are separated by one or more nucleobase(s) to which the ASO does not hybridize.

ASOs are polynucleotides made of nucleotides comprising a nucleobase that may be capable of hybridizing to a complementary nucleobase present on a target mRNA, a sugar moiety, and a backbone connecting the monomers. The term ASO also embodies any oligomeric molecule that comprises nucleobases capable of hybridizing to a complementary nucleobase on a target mRNA but does not comprise a sugar moiety, such as a peptide nucleic acid (PNA). The ASOs may be comprised of naturally-occurring nucleotides, nucleotide analogs, modified nucleotides, or any combination of two or three of the preceding. The term "naturally occurring nucleotides" includes deoxyribonucleotides and ribonucleotides. The term "modified nucleotides" includes nucleotides with modified or substituted sugar groups and/or having a modified backbone. Chemical modifications of ASOs or components of ASOs that are compatible with the methods and compositions described herein will be evident to one of skill in the art and can be found, for example, in U.S. Pat. No. 8,258,109 B2, U.S. Pat. No. 5,656,612, U.S. Patent Publication No. 2012/0190728 and Dias and Stein, *Mol. Cancer Ther.* 2002, 1, 347-355, herein incorporated by reference in their entirety.

The nucleobase of an ASO may be any naturally occurring, unmodified nucleobase such as adenine, guanine, cytosine, thymine and uracil or any synthetic or modified nucleobase that is sufficiently similar to an unmodified nucleobase such that it is capable of hydrogen bonding with a nucleobase present on a target mRNA. Examples of modified nucleobases include, without limitation, hypoxanthine, xanthine, 7-methylguanine, 5,6-dihydrouracil, 5-methylcytosine, and 5-hydroxymethoylcytosine.

Any of the ASOs described herein may contain a sugar moiety that comprises ribose or deoxyribose, as present in naturally occurring nucleotides, or a modified sugar moiety, including sugar moieties containing a morpholine ring. Non-limiting examples of modified sugar moieties include 2' substitutions such as 2'-O-methyl (2'OMe), 2'-O-methoxyethyl (2'MOE), 2'-O-aminoethyl, 2'F; N3'→P5' phosphoramidate, 2'dimethylaminooxyethoxy, 2'dimethylaminoethoxyethoxy, 2'-guanidinidium, 2'-O-guanidinium ethyl, carbamate modified sugars, and bicyclic modified sugars. In some embodiments, the sugar moiety modification is selected from 2'OMe, 2'F, and 2'MOE. In some embodiments, the sugar moiety modification is an extra bridge bond, such as in a locked nucleic acid (LNA).

The ASOs described herein also comprise a backbone structure that connects the components of an oligomer. The term "backbone structure" and "oligonucleotide linkages" may be used interchangeably and refer to the connection between monomers of the ASO. In naturally occurring oligonucleotides, the backbone comprises a 3'-5' phosphodiester linkage connecting sugar moieties of the oligomer. The backbone structure or oligonucleotide linkages of the ASO described herein may include (but are not limited to) phosphorothioate, phosphorodithioate, phosphoroselerloate, phosphorodiselenoate, phosphoroanilothioate, phoshoraniladate, phosphoronmidate, and the like. See e.g., LaPlanche et al. *Nucleic Acids Res.* 14:9081 (1986); Stec et al. *J. Am. Chem. Soc.* 106:6077 (1984), Stein et al. *Nucleic Acids Res.* 16:3209 (1988), Zon et al. *Anti Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990). In some embodiments, the backbone structure of the ASO does not contain phosphorous but rather contains peptide bonds, for example in a peptide nucleic acid (PNA), or linking groups including carbamate, amides, and linear and cyclic hydrocarbon groups. In some embodiments, the backbone modification is a phosphothioate linkage.

In some examples, each monomer of the ASO is unmodified or is modified in the same way, for example each linkage of the backbone of the ASO comprises a phosphorothioate linkage or each ribose sugar moiety comprises a 2'O-methyl modification. Such modifications that are present on each of the monomer components of an ASO are referred to as "uniform modifications." In some examples, a combination of different modifications may be desired, for example, an ASO may comprise a combination of phosphorodiamidate linkages and sugar moieties comprising morpholine rings (morpholinos). Combinations of different modifications to an ASO are referred to as "mixed modifications" or "mixed chemistries."

In some embodiments, the ASO comprises one or more backbone modification. In some embodiments, the ASO comprises one or more sugar moiety modification. In some embodiments, the ASO comprises one or more backbone modification and one or more sugar moiety modification. In some embodiments, the ASO comprises 2'MOE modifications and a phosphorothioate backbone. In some embodiments, the ASO comprises a phosphoamidate morpholino (PMO). In some embodiments, the ASO comprises a peptide nucleic acid (PNA). In some embodiments, the ASO comprises a ribofuransyl or 2'deoxyribofuransyl modification. In some embodiments, the ASO comprises 2'4'-constrained 2'O-methyloxyethyl (cMOE) modifications. In some embodiments, the ASO comprises cEt 2', 4' constrained 2'-O ethyl BNA modifications.

Any of the ASOs or any component of an ASO (e.g., a nucleobase, sugar moiety, backbone) described herein may be modified in order to achieve desired properties or activities of the ASO or reduce undesired properties or activities of the ASO. For example, an ASO or one or more component of any ASO may be modified to enhance binding affinity to a target sequence on a mRNA; reduce binding to any non-target sequence; reduce degradation by cellular nucleases (i.e., RNase H); improve uptake of the ASO into a cell and/or into the nucleus of a cell; alter the pharmacokinetics or pharmacodynamics of the ASO; and modulate the half-life of the ASO.

In some embodiments, the ASOs are comprised of 2'-O-(2-methoxyethyl) (MOE) phosphorothioate-modified nucleotides. ASOs comprised of such nucleotides are especially well-suited to the methods disclosed herein; oligonucleotides having such modifications have been shown to have significantly enhanced resistance to nuclease degradation and increased bioavailability, making them suitable, for example, for oral delivery in some embodiments described herein. See e.g., Geary et al., *J Pharmacol Exp Ther.* 2001; 296(3):890-7; Geary et al., *J Pharmacol Exp Ther.* 2001; 296(3):898-904.

Methods of synthesizing ASOs are known to one of skill in the art. Alternatively or in addition, ASOs may be obtained from a commercial source.

In some embodiments, the ASOs bind to or are specific to (e.g., bind in a gene-specific manner to) a region of a nucleic acid (e.g., mRNA) that is adjacent to and upstream of an exon-exon junction, such as to a region in which an EJC is typically bound. Unless specified otherwise, the left-hand end of single-stranded nucleic acid (e.g., mRNA, oligonucleotide, ASO etc.) sequences is the 5' end and the left-hand direction of single or double-stranded nucleic acid sequences is referred to as the 5' direction. Similarly, the right-hand end or direction of a nucleic acid sequence (single or double stranded) is the 3' end or direction. Generally, a region or sequence that is 5' to a reference point in a nucleic acid is referred to as "upstream," and a region or sequence that is 3' to a reference point in a nucleic acid is referred to as "downstream." Generally, an initiation or start codon is located near the 5' end and the termination codon is located near the 3' end. Nucleotides that are upstream of a reference point in a nucleic acid may be designated by a negative number; nucleotides that are downstream of a reference point may be designated by a positive number. For example, a reference point (e.g., an exon-exon junction in mRNA) may be designated as the "zero" site, and a nucleotide that is directly adjacent and upstream of the reference point is designated "minus one," e.g., "4," while a nucleotide that is directly adjacent and downstream of the reference point is designated "plus one," e.g., "+1." Thus, in some aspects, the ASOs are specific to a region in a nucleic acid (e.g., mRNA) that is 5' to an exon-exon junction in an mRNA (e.g., in the direction designated by negative numbers). For example, the ASOs are specific to any region of nucleic acid (e.g., mRNA) sequence within the first 100 nucleotides upstream of (5' to) an exon-exon junction (e.g., specific to a region between about nucleotides −1 and −100 relative to the exon-exon junction). In some aspects, the ASOs are specific to a region within approximately the first 90, 80, 70, 60, 50, 40, 30, 20, or 10 nucleotides upstream of an exon-exon junction (specific to a region designated −90, −80, −70, −60, −50, −40, −30, −20 or −10, relative to an exon-exon junction). In some embodiments the ASOs are specific to a region of the mRNA that is between about −6 and about −38 (with reference to an exon-exon junction). In some embodiments with reference to an exon-exon junction, the ASOs are specific to a region of the mRNA is that is between about −5 and about −40, about −7 and about −35, about −10 and about −30, about −15 and about −25, or about −18 and about −24. In some embodiments, the ASO is specific to a sequence that encompasses the region between about −20 and about −24, e.g., the region in which the EJC is typically bound. Using RNase H protection assays, EJC-protected areas were mapped in vitro to a region between −20 to −24 nt upstream of the 3' end of test exons (23). In addition, transcriptome-wide analyses of EJC deposition confirmed that the majority of the EJCs are deposited between −20 to −24 nucleotides upstream of each exon-exon junction.

For example, an ASO may be specific to a sequence (e.g., hybridizes to a target sequence) that completely or partially overlaps with a region between −20 and −24 (in reference to an exon-exon junction). In some embodiments, the ASO overlaps with a single nucleotide in the region between −20 and −24. In some embodiments, the ASO overlaps with at least 2 nucleotides, at least 3 nucleotides, at least 4 nucleotides, or with the 5 nucleotides or more in the region between −20 and −24.

The ASOs may be of any length suitable for specific binding and effective inhibition of EJC binding or deposition. For example, the ASO may be 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides in length. In some embodiments, the ASO is between about 10 and about 30, about 10 and about 20, or about 15 nucleotides in length. Generally, the ASO is designed to bind to a region upstream of an exon-exon junction and be of a certain length so as to specifically block EJC binding or deposition but not interfere with mRNA splicing. In some embodiments, two or more ASOs are designed and used to block EJC binding or deposition upstream of one or more exon-exon junction(s).

In some embodiments, the ASO binds a region upstream of an exon-exon junction that is located downstream of (3' to) a premature termination codon (PTC), such as a PTC resulting from a nonsense mutation in a particular gene or mRNA. In some embodiments, the PTC is a naturally occurring PTC, e.g., the PTC is not the result of a mutation. In some examples, the region that is targeted by the ASO is upstream of the first exon-exon junction that is downstream of the PTC. In other examples, regions upstream of one or more other exon-exon junctions are also targeted (e.g., as long as they are downstream of the PTC). In one embodiment, the region that is targeted is the region that, if bound by the ASO, inhibition or blocking of one or more components of the EJC occurs, and the region that, when otherwise bound by the EJC, is one that marks or signal the mRNA to be degraded by NMD. In another embodiment, the region that is targeted to block deposition of the EJC (by blocking the binding or formation of the EJC) is adjacent to the region that would otherwise be bound by the EJC. Thus, for example, and without being bound by any particular mechanism, binding or hybridizing of an ASO to an mRNA displaces, blocks, or otherwise prevents the EJC from binding to or forming on the mRNA in a functional manner (e.g., at a region that is located downstream of a PTC and upstream of an exon-exon junction), resulting in inhibition of NMD of the mRNA.

In some embodiments, the nucleic acid to be targeted by an ASO is an mRNA transcript expressed in a cell, such as a eukaryotic cell. As described herein, the mRNA contains a nonsense mutation, which results in a PTC. Typically, mRNAs with PTCs are targets of NMD. In some embodiments, the nonsense mutation is a disease-causing mutation (such as a disease-causing mutation described herein). The disease can be caused by the rapid turnover (e.g., by NMD) of the mRNA, a lack or reduced production of functional protein due to a truncated protein product, insufficient levels of a truncated protein product having normal or partial function, or combinations thereof.

By "mutation," it is meant that a particular nucleic acid (e.g., a gene, transcript expressed from such gene) differs by one or more nucleotides from a wild type nucleotide sequence and encodes one or more amino acid substitutions, additions, or in some cases, deletions or truncations, in the protein expressed therefrom. Mutations include, but are not limited to, point mutations (affecting a single nucleotide), nucleotide substitutions, insertions, deletions (including truncations), or combinations thereof. "Nonsense mutations" include any mutation that results in (premature) introduction of a stop (termination) codon upstream of the normal stop codon. Nonsense mutations, in some aspects, cause and are thus interchangeably referred to as "premature termination codons" (PTCs). In some aspects, PTCs comprise a triplet nucleotide sequence, for example UGA (e.g., TGA in DNA), UAG (e.g., TAG in DNA), or UAA (e.g., TAA in DNA). For example, mutations (e.g., in DNA, mRNA (RNA), or both) that result in a PTC include, but are not limited to: (1) single base pair substitutions that change a sense codon to an in-frame PTC (e.g., nonsense mutations); (2) insertion or deletion mutations that alter the ribosomal reading frame, causing translating ribosomes to encounter a PTC; (3) an insertion mutation that maintains the proper distal reading frame but introduces an in-frame PTC; and (4) mutations that lead to mRNA splicing defects that cause retention of an intron (or part of an intron) that alters the reading frame, leading translating ribosomes to encounter a PTC. In some aspects, mutations resulting in a PTC have important consequences on gene expression, such as in the context of disease. For example, a PTC will terminate mRNA translation prior to completion of a full-length polypeptide, leading to production of truncated proteins that are often nonfunctional and/or unstable and/or have detrimental function. In addition, PTC-containing mRNAs are also frequently unstable because the MRNAs are degraded by NMD, resulting in a severe reduction in steady-state mRNA levels. In some examples, the combination of these PTC-induced events reduce the level of functional protein produced to such an extent that a severe disease state results.

The following is a non-limiting list of sequences of ASOs for inhibiting NMD of mRNA transcribed from a HBB allele containing a nonsense mutation (e.g., CM810001, CM880039, CM034660, CM880040, and CM900122), for example in treating β-thalassemia:

```
                            (SEQ ID NO: 1)
GCAGCTTGTCACAGT;

(SEQ ID NO: 2)
TGCAGCTTGTCACAG;

(SEQ ID NO: 3)
GTGCAGCTTGTCACA;

(SEQ ID NO: 4)
CGTGCAGCTTGTCAC;

(SEQ ID NO: 5)
ACGTGCAGCTTGTCA;

(SEQ ID NO: 6)
CACGTGCAGCTTGTC;

(SEQ ID NO: 7)
CCACGTGCAGCTTGT;

(SEQ ID NO: 8)
TCCACGTGCAGCTTG;

(SEQ ID NO: 9)
ATCCACGTGCAGCTT;

(SEQ ID NO: 10)
GATCCACGTGCAGCT;

(SEQ ID NO: 11)
GGATCCACGTGCAGC;

(SEQ ID NO: 12)
AGGATCCACGTGCAG;

(SEQ ID NO: 13)
CAGGATCCACGTGCA;

(SEQ ID NO: 14)
TCAGGATCCACGTGC;

(SEQ ID NO: 15)
CTCAGGATCCACGTG;

(SEQ ID NO: 16)
TCTCAGGATCCACGT;

(SEQ ID NO: 17)
TTCTCAGGATCCACG;

(SEQ ID NO: 18)
GTTCTCAGGATCCAC;

(SEQ ID NO: 19)
AGTTCTCAGGATCCA.
```

The following is a non-limiting list of sequences of ASOs for inhibiting NMD of mRNA transcribed from a MECP2 allele containing a nonsense mutation (e.g., CM060329, CM023409, HM971529, CM010332, CM057720, CM010333, CM035705, CM055984, and CM076290), for example in treating Rett syndrome:

```
                            (SEQ ID NO: 20)
CCCAGCAGAGCGGCC;

(SEQ ID NO: 21)
TCCCAGCAGAGCGGC;

(SEQ ID NO: 22)
TTCCCAGCAGAGCGG;

(SEQ ID NO: 23)
CTTCCCAGCAGAGCG;

(SEQ ID NO: 24)
ACTTCCCAGCAGAGC;

(SEQ ID NO: 25)
TACTTCCCAGCAGAG;

(SEQ ID NO: 26)
ATACTTCCCAGCAGA;

(SEQ ID NO: 27)
CATACTTCCCAGCAG;

(SEQ ID NO: 28)
TCATACTTCCCAGCA;

(SEQ ID NO: 29)
ATCATACTTCCCAGC;

(SEQ ID NO: 30)
CATCATACTTCCCAG;

(SEQ ID NO: 31)
ACATCATACTTCCCA;

(SEQ ID NO: 32)
CACATCATACTTCCC;

(SEQ ID NO: 33)
ACACATCATACTTCC;

(SEQ ID NO: 34)
TACACATCATACTTC;

(SEQ ID NO: 35)
ATACACATCATACTT;

(SEQ ID NO: 36)
AATACACATCATACT;

(SEQ ID NO: 37)
AAATACACATCATAC;

(SEQ ID NO: 38)
CAAATACACATCATA.
```

The following is a non-limiting list of sequences of ASOs for inhibiting NMD of mRNA transcribed from a CFTR allele containing a nonsense mutation (e.g., CM960290, CM920186, CM993870, CM970297, CM900061, CM003260, CM993871, CM972963, CM920192, CM930137, CM900062, CM920194, CM024696, CM983581, CM983582, CM931253, and CM960291), for example in treating cystic fibrosis and/or CBAVD:

```
ASOs targeting exon 23
                            (SEQ ID NO: 39)
TCCTCCACTGTTGCA;

(SEQ ID NO: 40)
TTCCTCCACTGTTGC;
```

TTTCCTCCACTGTTG; (SEQ ID NO: 41)

CTTTCCTCCACTGTT; (SEQ ID NO: 42)

GCTTTCCTCCACTGT; (SEQ ID NO: 43)

GGCTTTCCTCCACTG; (SEQ ID NO: 44)

AGGCTTTCCTCCACT; (SEQ ID NO: 45)

AAGGCTTTCCTCCAC; (SEQ ID NO: 46)

AAAGGCTTTCCTCCA; (SEQ ID NO: 47)

CAAAGGCTTTCCTCC; (SEQ ID NO: 48)

CCAAAGGCTTTCCTC; (SEQ ID NO: 49)

TCCAAAGGCTTTCCT; (SEQ ID NO: 50)

CTCCAAAGGCTTTCC; (SEQ ID NO: 51)

ACTCCAAAGGCTTTC; (SEQ ID NO: 52)

CACTCCAAAGGCTTT; (SEQ ID NO: 53)

TCACTCCAAAGGCTT; (SEQ ID NO: 54)

ATCACTCCAAAGGCT; (SEQ ID NO: 55)

TATCACTCCAAAGGC; (SEQ ID NO: 56)

GTATCACTCCAAAGG. (SEQ ID NO: 57)

ASOs targeting exon 24

CTTGATCACTCCACT; (SEQ ID NO: 58)

TCTTGATCACTCCAC; (SEQ ID NO: 59)

TTCTTGATCACTCCA; (SEQ ID NO: 60)

TTTCTTGATCACTCC; (SEQ ID NO: 61)

ATTTCTTGATCACTC; (SEQ ID NO: 62)

TATTTCTTGATCACT; (SEQ ID NO: 63)

ATATTTCTTGATCAC; (SEQ ID NO: 64)

CATATTTCTTGATCA; (SEQ ID NO: 65)

CCATATTTCTTGATC; (SEQ ID NO: 66)

TCCATATTTCTTGAT; (SEQ ID NO: 67)

TTCCATATTTCTTGA; (SEQ ID NO: 68)

TTTCCATATTTCTTG; (SEQ ID NO: 69)

CTTTCCATATTTCTT; (SEQ ID NO: 70)

ACTTTCCATATTTCT; (SEQ ID NO: 71)

AACTTTCCATATTTC; (SEQ ID NO: 72)

CAACTTTCCATATTT; (SEQ ID NO: 73)

GCAACTTTCCATATT; (SEQ ID NO: 74)

TGCAACTTTCCATAT; (SEQ ID NO: 75)

CTGCAACTTTCCATA. (SEQ ID NO: 76)

ASOs targeting exon 25

TTCATCAAGCAGCAA; (SEQ ID NO: 77)

GTTCATCAAGCAGCA; (SEQ ID NO: 78)

GGTTCATCAAGCAGC; (SEQ ID NO: 79)

GGGTTCATCAAGCAG; (SEQ ID NO: 80)

TGGGTTCATCAAGCA; (SEQ ID NO: 81)

CTGGGTTCATCAAGC; (SEQ ID NO: 82)

ACTGGGTTCATCAAG; (SEQ ID NO: 83)

CACTGGGTTCATCAA; (SEQ ID NO: 84)

GCACTGGGTTCATCA, (SEQ ID NO: 85)

AGCACTGGGTTCATC; (SEQ ID NO: 86)

GAGCACTGGGTTCAT; (SEQ ID NO: 87)

TGAGCACTGGGTTCA; (SEQ ID NO: 88)

ATGAGCACTGGGTTC; (SEQ ID NO: 89)

AATGAGCACTGGGTT; (SEQ ID NO: 90)

AAATGAGCACTGGGT; (SEQ ID NO: 91)

CAAATGAGCACTGGG; (SEQ ID NO: 92)

CCAAATGAGCACTGG; (SEQ ID NO: 93)

TCCAAATGAGCACTG; (SEQ ID NO: 94)

ASOs targeting exon 26

TTGCTTCTATCCTGT;  (SEQ ID NO: 96)

ATTGCTTCTATCCTG;  (SEQ ID NO: 97)

CATTGCTTCTATCCT;  (SEQ ID NO: 98)

GCATTGCTTCTATCC;  (SEQ ID NO: 99)

AGCATTGCTTCTATC;  (SEQ ID NO: 100)

CAGCATTGCTTCTAT;  (SEQ ID NO: 101)

CCAGCATTGCTTCTA;  (SEQ ID NO: 102)

TCCAGCATTGCTTCT;  (SEQ ID NO: 103)

TTCCAGCATTGCTTC;  (SEQ ID NO: 104)

ATTCCAGCATTGCTT;  (SEQ ID NO: 105)

CATTCCAGCATTGCT;  (SEQ ID NO: 106)

GCATTCCAGCATTGC;  (SEQ ID NO: 107)

GGCATTCCAGCATTG;  (SEQ ID NO: 108)

TGGCATTCCAGCATT;  (SEQ ID NO: 109)

TTGGCATTCCAGCAT;  (SEQ ID NO: 110)

GTTGGCATTCCAGCA;  (SEQ ID NO: 111)

TGTTGGCATTCCAGC;  (SEQ ID NO: 112)

TTGTTGGCATTCCAG,  (SEQ ID NO: 113)

ATTGTTGGCATTCCA.  (SEQ ID NO: 114)

The following is a non-limiting list of sequences of ASOs for inhibiting NMD of mRNA transcribed from a DMD allele containing a nonsense mutation (e.g., CM054661, CM960494, CM040028, CM084901, CM043277, CM950349, CM070908, and CM022961), for example in treating DMD/BMD:

ASOs targeting exon 74

TAGGATTCTCTCTAG;  (SEQ ID NO: 115)

CTAGGATTCTCTCTA;  (SEQ ID NO: 116)

GCTAGGATTCTCTCT;  (SEQ ID NO: 117)

TGCTAGGATTCTCTC;  (SEQ ID NO: 118)

CTGCTAGGATTCTCT;  (SEQ ID NO: 119)

TCTGCTAGGATTCTC;  (SEQ ID NO: 120)

ATCTGCTAGGATTCT;  (SEQ ID NO: 121)

GATCTGCTAGGATTC;  (SEQ ID NO: 122)

AGATCTGCTAGGATT;  (SEQ ID NO: 123)

AAGATCTGCTAGGAT;  (SEQ ID NO: 124)

CAAGATCTGCTAGGA;  (SEQ ID NO: 125)

TCAAGATCTGCTAGG;  (SEQ ID NO: 126)

CTCAAGATCTGCTAG;  (SEQ ID NO: 127)

CCTCAAGATCTGCTA;  (SEQ ID NO: 128)

TCCTCAAGATCTGCT;  (SEQ ID NO: 129)

TTCCTCAAGATCTGC;  (SEQ ID NO: 130)

CTTCCTCAAGATCTG;  (SEQ ID NO: 131)

TCTTCCTCAAGATCT;  (SEQ ID NO: 132)

TTCTTCCTCAAGATC.  (SEQ ID NO: 133)

ASOs targeting exon 75

TGTGTAACTGTGACT;  (SEQ ID NO: 134)

CTGTGTAACTGTGAC;  (SEQ ID NO: 135)

CCTGTGTAACTGTGA;  (SEQ ID NO: 136)

GCCTGTGTAACTGTG;  (SEQ ID NO: 137)

AGCCTGTGTAACTGT;  (SEQ ID NO: 138)

TAGCCTGTGTAACTG;  (SEQ ID NO: 139)

TTAGCCTGTGTAACT;  (SEQ ID NO: 140)

CTTAGCCTGTGTAAC;  (SEQ ID NO: 141)

CCTTAGCCTGTGTAA;  (SEQ ID NO: 142)

GCCTTAGCCTGTGTA;  (SEQ ID NO: 143)

TGCCTTAGCCTGTGT;  (SEQ ID NO: 144)

(Previous continued line:)
ATCCAAATGAGCACT.  (SEQ ID NO: 95)

CTGCCTTAGCCTGTG; (SEQ ID NO: 145)

GCTGCCTTAGCCTGT; (SEQ ID NO: 146)

AGCTGCCTTAGCCTG; (SEQ ID NO: 147)

CAGCTGCCTTAGCCT; (SEQ ID NO: 148)

GCAGCTGCCTTAGCC; (SEQ ID NO: 149)

AGCAGCTGCCTTAGC; (SEQ ID NO: 150)

CAGCAGCTGCCTTAG; (SEQ ID NO: 151)

CCAGCAGCTGCCTTA. (SEQ ID NO: 152)

ASOs targeting exon 76

CCAACCACTCGGAGC; (SEQ ID NO: 153)

GCCAACCACTCGGAG; (SEQ ID NO: 154)

TGCCAACCACTCGGA; (SEQ ID NO: 155)

CTGCCAACCACTCGG; (SEQ ID NO: 156)

ACTGCCAACCACTCG; (SEQ ID NO: 157)

GACTGCCAACCACTC; (SEQ ID NO: 158)

TGACTGCCAACCACT; (SEQ ID NO: 159)

TTGACTGCCAACCAC; (SEQ ID NO: 160)

TTTGACTGCCAACCA; (SEQ ID NO: 161)

GTTTGACTGCCAACC; (SEQ ID NO: 162)

AGTTTGACTGCCAAC; (SEQ ID NO: 163)

AAGTTTGACTGCCAA; (SEQ ID NO: 164)

GAAGTTTGACTGCCA; (SEQ ID NO: 165)

CGAAGTTTGACTGCC; (SEQ ID NO: 166)

CCGAAGTTTGACTGC; (SEQ ID NO: 167)

TCCGAAGTTTGACTG; (SEQ ID NO: 168)

GTCCGAAGTTTGACT; (SEQ ID NO: 169)

AGTCCGAAGTTTGAC; (SEQ ID NO: 170)

GAGTCCGAAGTTTGA. (SEQ ID NO: 171)

ASOs targeting exon 77

TTGAGTTGCTCCATC; (SEQ ID NO: 172)

GTTGAGTTGCTCCAT; (SEQ ID NO: 173)

TGTTGAGTTGCTCCA; (SEQ ID NO: 174)

TTGTTGAGTTGCTCC; (SEQ ID NO: 175)

GTTGTTGAGTTGCTC; (SEQ ID NO: 176)

AGTTGTTGAGTTGCT; (SEQ ID NO: 177)

GAGTTGTTGAGTTGC; (SEQ ID NO: 178)

GGAGTTGTTGAGTTG; (SEQ ID NO: 179)

AGGAGTTGTTGAGTT; (SEQ ID NO: 180)

AAGGAGTTGTTGAGT; (SEQ ID NO: 181)

GAAGGAGTTGTTGAG; (SEQ ID NO: 182)

GGAAGGAGTTGTTGA; (SEQ ID NO: 183)

GGGAAGGAGTTGTTG; (SEQ ID NO: 184)

AGGGAAGGAGTTGTT; (SEQ ID NO: 185)

TAGGGAAGGAGTTGT; (SEQ ID NO: 186)

CTAGGGAAGGAGTTG; (SEQ ID NO: 187)

ACTAGGGAAGGAGTT; (SEQ ID NO: 188)

AACTAGGGAAGGAGT; (SEQ ID NO: 189)

GAACTAGGGAAGGAG. (SEQ ID NO: 190)

The following is a non-limiting list of sequences of ASOs for inhibiting NMD of mRNA transcribed from a IDUA allele containing a nonsense mutation (e.g., CM920372), for example in treating MPS1-H:

ASOs targeting exon 9

AGCCGCAGGGTCACC; (SEQ ID NO: 191)

CAGCCGCAGGGTCAC; (SEQ ID NO: 192)

GCAGCCGCAGGGTCA; (SEQ ID NO: 193)

CGCAGCCGCAGGGTC; (SEQ ID NO: 194)

GCGCAGCCGCAGGGT; (SEQ ID NO: 195)

CGCGCAGCCGCAGGG; (SEQ ID NO: 196)

CCGCGCAGCCGCAGG; (SEQ ID NO: 197)

CCCGCGCAGCCGCAG; (SEQ ID NO: 198)

CCCCGCGCAGCCGCA; (SEQ ID NO: 199)

ACCCCGCGCAGCCGC; (SEQ ID NO: 200)

CACCCCGCGCAGCCG; (SEQ ID NO: 201)

GCACCCCGCGCAGCC; (SEQ ID NO: 202)

GGCACCCCGCGCAGC; (SEQ ID NO: 203)

GGGCACCCCGCGCAG (SEQ ID NO: 204)

ASOs targeting exon 10

ACTGCTCTGCCGTGG; (SEQ ID NO: 205)

AACTGCTCTGCCGTG; (SEQ ID NO: 206)

GAACTGCTCTGCCGT; (SEQ ID NO: 207)

GGAACTGCTCTGCCG; (SEQ ID NO: 208)

CGGAACTGCTCTGCC; (SEQ ID NO: 209)

CCGGAACTGCTCTGC; (SEQ ID NO: 210)

GCCGGAACTGCTCTG; (SEQ ID NO: 211)

CGCCGGAACTGCTCT; (SEQ ID NO: 212)

GCGCCGGAACTGCTC; (SEQ ID NO: 213)

TGCGCCGGAACTGCT; (SEQ ID NO: 214)

ATGCGCCGGAACTGC; (SEQ ID NO: 215)

CATGCGCCGGAACTG; (SEQ ID NO: 216)

GCATGCGCCGGAACT; (SEQ ID NO: 217)

CGCATGCGCCGGAAC; (SEQ ID NO: 218)

GCGCATGCGCCGGAA; (SEQ ID NO: 219)

CGCGCATGCGCCGGA; (SEQ ID NO: 220)

GCGCGCATGCGCCGG; (SEQ ID NO: 221)

CGCGCGCATGCGCCG; (SEQ ID NO: 222)

CCGCGCGCATGCGCC (SEQ ID NO: 223)

ASOs targeting exon 11

GCGCACACACGTGCA; (SEQ ID NO: 224)

CGCGCACACACGTGC; (SEQ ID NO: 225)

GCGCGCACACACGTG; (SEQ ID NO: 226)

GGCGCGCACACACGT; (SEQ ID NO: 227)

GGGCGCGCACACACG; (SEQ ID NO: 228)

GGGCGGCTTCTCGGG; (SEQ ID NO: 229)

CGGGCGGCTTCTCGG (SEQ ID NO: 230)

ASOs targeting exon 12

CCAGACCAGAACCAG; (SEQ ID NO: 231)

ACCAGACCAGAACCA; (SEQ ID NO: 232)

GACCAGACCAGAACC; (SEQ ID NO: 233)

CGACCAGACCAGAAC; (SEQ ID NO: 234)

CCGACCAGACCAGAA; (SEQ ID NO: 235)

TCCGACCAGACCAGA; (SEQ ID NO: 236)

ATCCGACCAGACCAG; (SEQ ID NO: 237)

CATCCGACCAGACCA; (SEQ ID NO: 238)

TCATCCGACCAGACC; (SEQ ID NO: 239)

TTCATCCGACCAGAC; (SEQ ID NO: 240)

GTTCATCCGACCAGA; (SEQ ID NO: 241)

TGTTCATCCGACCAG; (SEQ ID NO: 242)

GTGTTCATCCGACCA; (SEQ ID NO: 243)

CGTGTTCATCCGACC; (SEQ ID NO: 244)

ACGTGTTCATCCGAC; (SEQ ID NO: 245)

CACGTGTTCATCCGA; (SEQ ID NO: 246)

CCACGTGTTCATCCG; (SEQ ID NO: 247)

CCCACGTGTTCATCC; (SEQ ID NO: 248)

-continued

GCCCACGTGTTCATC (SEQ ID NO: 249)

ASOs targeting exon 13

AAGGTCGATGGCTTC; (SEQ ID NO: 250)

GAAGGTCGATGGCTT; (SEQ ID NO: 251)

TGAAGGTCGATGGCT; (SEQ ID NO: 252)

TTGAAGGTCGATGGC; (SEQ ID NO: 253)

GTTGAAGGTCGATGG; (SEQ ID NO: 254)

GGTTGAAGGTCGATG; (SEQ ID NO: 255)

AGGTTGAAGGTCGAT; (SEQ ID NO: 256)

GAGGTTGAAGGTCGA; (SEQ ID NO: 257)

AGAGGTTGAAGGTCG; (SEQ ID NO: 258)

AAGAGGTTGAAGGTC; (SEQ ID NO: 259)

AAAGAGGTTGAAGGT; (SEQ ID NO: 260)

CAAAGAGGTTGAAGG; (SEQ ID NO: 261)

ACAAAGAGGTTGAAG; (SEQ ID NO: 262)

CACAAAGAGGTTGAA; (SEQ ID NO: 263)

ACACAAAGAGGTTGA; (SEQ ID NO: 264)

AACACAAAGAGGTTG; (SEQ ID NO: 265)

GAACACAAAGAGGTT; (SEQ ID NO: 266)

TGAACACAAAGAGGT; (SEQ ID NO: 267)

CTGAACACAAAGAGG (SEQ ID NO: 268)

Also described is an (at least one, one or more) antisense oligonucleotide (ASO) for use in a method of inhibiting nonsense-mediated decay (NMD) of mRNA in a gene-specific manner in a eukaryotic cell, wherein said eukaryotic cell comprises mRNA encoded by a nucleic acid that contains a disease-causing premature termination codon (PTC) or a naturally-occurring premature termination codon (PTC), said method comprising contacting said eukaryotic cell with said ASO, wherein the ASO hybridizes to a region of the mRNA that is from about 1 to about 50 nucleotides upstream of an exon-exon junction that: (i) is located downstream from the PTC; and (ii) when marked by deposition of exon junction complexes (EJC), marks the mRNA for nonsense-mediated decay, under conditions wherein the ASO enters the cell in sufficient quantity to inhibit deposition of EJC at the exon-exon junction and inhibit NMD of the mRNA that contains the PTC.

Further described is an (at least one, one or more) antisense oligonucleotide (ASO) for use in a method of inhibiting deposition of exon junction complexes (EJC) in a gene-specific manner in a eukaryotic cell, comprising introducing said ASO into the cell, wherein the ASO is specific to mRNA from about 1 to about 50 nucleotides upstream of an exon-exon junction that is: (i) downstream of a disease-causing or naturally occurring premature termination codon (PTC) in mRNA transcribed in the eukaryotic cell; and (ii) bound by exon junction complex (EJC) that identifies the mRNA for nonsense-mediated decay (NMD), whereby the ASO blocks binding or deposition of EJC to the exon-exon junction.

Another embodiment is an (at least one, one or more) antisense oligonucleotide (ASO) for use in a method of increasing the production in a eukaryotic cell of a truncated protein encoded by a gene that contains a premature termination codon (PTC), the method comprising introducing said ASO into the cell, wherein the ASO is specific to a region of the mRNA that is from about 1 to about 50 nucleotides upstream of an exon-exon junction that is downstream of a disease-causing or naturally occurring PTC in mRNA transcribed in the eukaryotic cell and to which deposition of exon junction complexes (EJC) marks the mRNA for nonsense-mediated decay, whereby the ASO enters the cell in sufficient quantity to inhibit deposition of EJC upstream of the exon-exon junction and inhibit NMD of mRNA that contains the PTC, whereby protein production occurs.

The disclosure also relates to an (at least one, one or more) antisense oligonucleotide (ASO) for use in a method of increasing the efficacy of a readthrough drug in a eukaryotic cell, wherein said ASO is specific to a region of mRNA transcribed in the eukaryotic cell that is from about 1 to about 50 nucleotides upstream of an exon-exon junction that is downstream of a disease-causing or naturally occurring premature termination codon (PTC) in said mRNA and to which deposition of exon junction complexes (EJC) marks the mRNA for nonsense-mediated decay, whereby the ASO enters the cell in sufficient quantity to inhibit deposition of EJC at the exon-exon junction and inhibit NMD of mRNA that contains the PTC and protein production occurs.

An (at least one, one or more) antisense oligonucleotide (ASO) for use in a method of treating a disease caused by a mutation that introduces a premature termination codon (PTC) in an mRNA, thereby producing PTC-containing mRNA, wherein said ASO inhibits NMD of the PTC-containing mRNA is also described.

A further embodiment is an (at least one, one or more) antisense oligonucleotide (ASO) for use in a method of treating a disease associated with a premature termination codon (PTC) in a subject, wherein said ASO hybridizes to a region of mRNA in said subject that is: (a) from about 1 to about 50 nucleotides upstream of an exon-exon junction located downstream from said PTC; and (b) marked for nonsense-mediated decay by deposition of exon junction complexes (EJC). According to one such use, the ASO can inhibit deposition of said EJC. In further embodiments, the ASO inhibits NMD of PTC-containing mRNA in the subject or the ASO increases the amount of a truncated protein encoded by a gene that contains said PTC. In any of the embodiments for use in treating a disease associated with a PTC, the PTC can arise from a mutation in said subject. The disease is selected from: Rett syndrome, cystic fibrosis, β-thalassemia, CBAVD, dystrophinopathy and Duchenne/Becker muscular dystrophy.

Also described is use of an ASO for use in the manufacture of a medicament, which is, in turn, for use in a method as defined in any one of the claims presented.

Methods

In some embodiments, a method for inhibiting NMD of mRNA in a gene-specific manner is provided. The term "gene-specific," means that the method inhibits NMD of mRNA expressed from a specific or particular gene, such as a gene that contains a disease-causing mutation (e.g., a nonsense mutation), as described herein. In some embodiments, the gene contains a PTC that is naturally occurring, e.g., the PTC is not the result of a mutation. Typically, the method involves inhibiting NMD of mRNA in a cell, such as a eukaryotic cell. However, in some aspects the method comprises inhibiting NMD of mRNA in a cell lysate or an in vitro reconstituted system, e.g., for the study of NMD and NMD inhibition.

In some embodiments, the method involves contacting a cell with an ASO capable of inhibiting NMD of mRNA (an ASO that inhibits NMD of mRNA), as described herein. The term "contacting" as used herein refers to exposing a cell to the ASO in such a manner or under such conditions that the ASO enters the cell. See, for example Juliano et al., *Bioconjug Chem.* 2012 Feb. 15; 23(2):147-57 (incorporated herein in its entirety). The ASO is delivered to the interior of the cell and enters the cell nucleus. In one embodiment, the cell is contacted with a vector (e.g., a viral genome, a plasmid, an artificial chromosome) that enters the cell. In the cell, the vector causes expression of the ASO in the cell, e.g., from the cellular genome or from an exogenous nucleic acid. ASO can be introduced into cells in vivo or ex vivo (in which case the resulting cells are introduced into an individual in need of therapy). The individual can be a human, a nonhuman mammal, other vertebrate, or plant. ASOs can be provided to an individual by any of a variety of methods, such as those described by Juliano et al. referenced above, such as delivery of "free" or "naked" ASOs which are taken up by some cells, delivery of ASOs conjugated to cell penetrating peptides (CPPs, e.g., TAT and Antennapedia peptides), delivery of ASOs conjugated to ligands for cell receptor uptake (e.g., ASO-cholesterol conjugates, ASO-folate conjugates, N-acetyl galactosamine conjugates, ASO-insulin-like growth factor 1 conjugates, ASO-RGD peptide conjugates, ASO-bombesin conjugates, etc.), delivery of ASOs associated with nanocarriers (e.g., lipid-based carriers, ASOs associated with perfluorocarbon nanoparticles, ASO-antibody conjugates, etc.). Other methods for delivery of nucleic acids such as ASOs are known in the art, and include, but are not limited to, forming nucleic acid conjugates with cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octa-decylamine or hexylamino-carbonyl-oxycholesterol moiety (Crooke et al., *J. Pharmacol. Exp. Ther.*, 1996, 277, 923-937).

The ASO enters the cell in sufficient quantity to inhibit or block deposition or binding of EJC at an exon-exon junction (e.g., in an mRNA containing a PTC, as described herein) in the nucleus, and inhibit NMD. While not being bound by theory, it is believed that the ASO binds to an mRNA and blocks deposition of the EJC in the nucleus. However, the ASO may compete with the EJC for binding (or components thereof) and/or displace the EJC (or components thereof) in the cytoplasm. As used herein, the term "inhibiting NMD" means reducing (partially or completely) the extent to which NMD occurs. Inhibition of NMD results in an increase in levels of an mRNA (e.g., a measurable increase in the level or amount of a particular mRNA). For instance, inhibiting NMD of a PTC-containing HBB mRNA results in a measurable increase in the amount of total HBB mRNA. Inhibition of NMD results in an increase in mRNA levels of 5% or more, such as 9%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 550%, 600%, 650%, 700%, 750%, 800%, 850%, 900%, 1000%, 1500%, 2000%, 2500%, 3000%, 3500%, 4000%, 4500%, 5000% or more, compared to mRNA levels in the absence of the ASO/absence of treatment (e.g., cytoplasmic levels of the PTC containing mRNA wherein no ASO is present in the cell). Inhibition of NMD results in an increase in mRNA levels of 5% or more, such as 9%, 10%, 15%, 20%, 25%, 30%, 35%, 40%, 45%, 50%, 55%, 60%, 65%, 70%, 75%, 80%, 85%, 90%, 95%, 100% of wild type mRNA levels (e.g., levels of cytoplasmic wild-type mRNA wherein the gene/mRNA does not contain a nonsense mutation). Inhibition of NMD can result in mRNA levels that are greater than wildtype levels. In some embodiments, inhibition of NMD results in a measurable increase of between 20% and 40%. Inhibition of NMD results in an increase of 1.01-, 1.05-, 1.10-, 1.25-, 1.50-, 2.0-, 2.5-, 3.0-, 3.5-, 4.0-, 4.5-, 5.0-, 5.5-, 6.0-, 6.5-, 7.0-, 7.5-, 8.0-, 8.5-, 9.0-, 9.5-, 10-, 15-, 20-, 25-, 30-, 35-, 40-, 45-, 50-, 55-, 60-, 65-, 70-, 75-, 80-, 85-, 90-, 95-, 100-fold or more in mRNA levels, as compared to mRNA levels in the absence of the ASO/absence of treatment (e.g., cytoplasmic levels of the PTC-containing mRNA wherein no ASO is present in the cell) or wild-type levels. Methods for measuring or quantifying mRNA levels are well known in the art, and include, for example, RT-PCR, RT-qPCR, microarray analysis, northern blot analysis, RNase-protection analysis, or any other suitable method, for example as described in Rio, D.C., RNA: *A Laboratory Manual*, Cold Spring Harbor Laboratory Press, 2011 (incorporated herein in its entirety).

Inhibition of NMD results in an increase of the level of protein (e.g., as encoded by HBB, MECP2, CFTR, DMD, IDUA etc.), for example the level of a protein product of an mRNA containing a PTC that was targeted by an ASO. For instance, inhibiting NMD of a PTC-containing HBB mRNA results in a measurable increase in the amount of total protein translated from the HBB mRNA. The protein product may be a truncated or full-length protein. In some aspects, inhibition of NMD results in an increase in mRNA levels of 5% or more, such as 9%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300%, 350%, 400%, 450%, 500%, 550%, 600%, 650%, 700%, 750%, 800%, 850%, 900%, 1000%, 1500%, 2000%, 2500%, 3000%, 3500%, 4000%, 4500%, 5000% or more, compared to protein levels in the absence of the ASO/absence of treatment (e.g., levels of expression of the truncated protein wherein no ASO is present in the cell) or wild-type levels (e.g., levels of expression of the wild-type protein wherein the gene/mRNA does not contain a nonsense mutation). In some aspects, inhibition of NMD results in a 1.01-, 1.05, 1.10-, 1.25-, 1.50-, 2.0-, 2.5-, 3.0-, 3.5-, 4.0-, 4.5-, 5.0-, 5.5-, 6.0-, 6.5-, 7.0-, 7.5-, 8.0-, 8.5-, 9.0-, 9.5-, 10-, 15-, 20-, 25-, 30-, 35-, 40-, 45-, 50-, 55-, 60-, 65-, 70-, 75-, 80-, 85-, 90-, 95-, 100- or more fold increase in protein levels, as compared to the protein levels in the absence of the ASO/absence of treatment or wild-type levels. Methods of measuring or quantifying protein levels are well known in the art, and include, for example, western blot analysis, immunocytochemistry, flow cytometry, mass spectrometry, or any other suitable method, for example as described in Link, A. J., *Proteomics: A Cold Spring Harbor Laboratory Course Manual*, Cold Spring Harbor Laboratory Press, 2009 (incorporated herein in its entirety).

In another embodiment, the method is a method of inhibiting deposition (e.g., by inhibiting binding or formation) of exon junction complexes (EJCs) in a gene-specific manner. The method comprises identifying an exon-exon junction that is downstream of a PTC in mRNA transcribed from a gene, e.g., a disease-causing nonsense mutant gene (e.g., HBB, CFTR, MECP2, DMD, IDUA) or a gene containing a naturally occurring PTC (e.g., as described herein), and introducing into the cell (e.g., by contacting the cell with) an ASO specific to the mRNA under conditions under which blocking of binding to or deposition of the EJC at the identified exon-exon junction occurs. In one embodiment, the identified exon-exon junction is one that, when bound by an EJC, identifies or marks the mRNA for NMD, for example as described herein. In another embodiment, the exon-exon junction is one that, when bound, does not identify or mark the mRNA for NMD. By an exon-exon junction "bound by an EJC," it is meant that the EJC is bound adjacent to and upstream of the junction, as described herein. In some aspects, the method involves identifying one or more exon-exon junctions bound by EJC. Methods for identifying exon-exon junctions (bound by EJC) are known, and include, for example, those described in the Examples section, e.g., RNA immunoprecipitation (RIP) or CLIP-seq. See also Seth et al., *Cold Spring Harbor Protoc.* 2009 June; 2009(6):pdb.prot5234 (incorporated herein in its entirety). Typically, a sufficient quantity (e.g., as described herein) of the ASO is introduced so as to block binding or deposition of the EJC to the exon-exon junction. In one example, a sufficient quantity to block EJC deposition can be determined based on RIP analysis, as described herein.

In another embodiment, a method of increasing the amount of a truncated protein encoded by a gene that contains a nonsense mutation (e.g., a disease-causing nonsense mutation), or a gene containing a naturally occurring PTC (e.g., as described herein) is provided. In some examples, the truncated protein expressed from the gene or mRNA containing the nonsense mutation is still functional, but, due to the PTC resulting from the nonsense mutation, some of the mRNA is degraded (by NMD) and only a small amount of the truncated protein is produced, leading to a disease state (e.g., as a result of insufficient quantities of the protein). Thus, in some aspects it is beneficial to block or inhibit NMD of the mRNA expressed from such a gene, thereby increasing the levels of available mRNA and resulting in increased levels of the functional truncated protein. For example, the Ullrich disease phenotype is caused by a deficiency in the collagen VI α2 protein. Partial NMD inhibition (in this case globally) was found to restore adequate levels of the truncated collagen protein to assemble with other collagen fibers, leading to partial restoration of a functional extracellular matrix in human fibroblasts (Usuki et al., *Ann Neurol.* 2004, 55:740-744; Usuki et al., *Mol. Ther.* 2006, 14:351-360).

The method involves identifying an exon-exon junction that is downstream of a PTC in an mRNA, such as mRNA transcribed in a eukaryotic cell (e.g., a human cell, such as those within an individual human), as described herein. The method further involves introducing into the eukaryotic cell an ASO specific to a region of the mRNA that is upstream of the identified exon-exon junction, e.g., as described herein. The method is carried out under conditions under which the ASO enters the cell (e.g., the nucleus of the cell) in sufficient quantity to inhibit deposition of EJC upstream of the identified exon-exon junction (e.g., as described herein), and inhibit NMD of the mRNA, resulting in increased protein production, e.g., increased levels of the truncated protein. In some embodiments, an effective amount of the ASO is introduced, delivered, or administered, as described herein, so as to increase levels of the truncated protein in amounts sufficient to ameliorate a disease state (e.g., a disease state caused by insufficient levels of a protein, truncated or otherwise, due to the presence of a PTC in the gene/mRNA encoding the protein).

In some embodiments, the method further involves contacting, introducing, delivering, or administering to the cell (e.g., as described herein) one or more drugs or compounds that promote readthrough of the PTC. By "promoting readthrough," it is meant that the drug or compound affects translation of a PTC containing mRNA, resulting in the incorporation of an amino acid at the PTC in the nascent growing polypeptide chain, rather than termination of translation and generation of a truncated protein, which would otherwise occur). For example, readthrough drugs, in some cases, enhance the ability of near-cognate aminoacyl tRNAs to compete with the release factor complex for binding PTCs in the ribosomal A site. By increasing the frequency at which PTCs are recoded into sense codons, enough full-length, functional protein may be produced to provide a therapeutic benefit to individuals who carry disease-causing nonsense mutations, as described herein. Methods for determining whether a drug is promoting readthrough are known in the art, and include, for example, western blot analysis, immunohistochemistry, flow cytometry, as well as cell-based reporter assays such as those described in the Examples section. In some aspects, improvement in one or more clinical parameters allows for determining whether a readthrough drug is effectively increasing levels of full-length protein. In some aspects, even modest or slight increases in the amount of full-length protein are beneficial in alleviating some disease states. For example, the lysosomal storage disease mucopolysaccharidosis type I-Hurler (MPS I-H, caused by nonsense mutation resulting in decreased levels of iduronidase), has a low threshold for correction, since <1% of wild-type iduronidase function can significantly moderate the clinical phenotype (Ashton et al., *Am. J. Hum. Genet.* 1992, 50: 787-794, Bunge et al., *Biochim. Biophys. Acta.* 1998, 1407: 249-256). Thus, increasing the amount of full-length protein, in some aspects, to reach 1% of wild-type levels, is beneficial in treating some diseases caused by nonsense mutations. In some examples, the method results in an increase of at least 5%, such as 9%, 10%, 15%, 20%, 25%, 30%, 35%, 40%, 45%, 50%, 55%, 60%, 65%, 70%, 75%, 80%, 85%, 90%, 95%, 99%, or a 100% increase, in the amount of full length protein produced, for example as compared to wild-type levels (e.g., levels of expression of the wild type protein wherein the gene/mRNA does not contain a nonsense mutation). In other examples, such as the disease β-thalassemia, increased levels of the full-length beta chains of hemoglobin leads to improved or ameliorated disease states, such as decreased or no anemia, decreased tiredness, decreased breathlessness, and increased exercise tolerance. Methods for monitoring improvement in the β-thalassemia disease state are known, and include, for example, pulse oximetry, hemoglobin electrophoresis; serum transferrin, ferritin, Fe binding capacity analysis; urine urobilin & urobilinogen assays; peripheral blood smear test; hematocrit analysis; and serum bilirubin analysis.

In some embodiments, the readthrough drug is ataluren (PTC124, PTC Therapeutics, South Plainfield, N.J.), or an aminoglycoside (e.g., drugs that generally consist of two to three aminosugars joined to a 2-deoxystreptamine ring by glycosidic linkages), such as amikacin, arbekacin, gentamicin, kanamycin, neomycin, netilmicin, paromomycin, rhodostreptomycin, streptomycin, tobramycin, apramycin, G418 (geneticin), and lividomycin, or salts and derivatives thereof. However, at certain doses, these drugs have been shown to be toxic. Thus in some aspects, the readthrough drug is an aminoglycoside analog having lower or no toxicity, for example NB30, a derivative of paromomycin; NB54, which combines components of paromomycin and amikacin; and NB84, which is composed of structural elements from paromomycin, amikacin, and G418. These compounds show more than a 10-fold reduction in cellular toxicity compared to the classical aminoglycosides, and each of the compounds was found to restore a significant amount of functional protein in mammalian cells carrying PTCs related to Usher syndrome, Rett syndrome, cystic fibrosis, and mucopolysaccharidosis I-Hurler (MPS I-H) (16). Other drugs or compounds that promote readthrough include the dipeptide antibiotic negamycin, as well as compounds identified in a screen performed by Du et al., (*J. Exp. Med.* 2009; 206(10):2285-97), e.g., N-(sec-butyl)-N'-phenylthiourea; 1,2-di-2-furyl-2-hydroxyethanone; 1-methyl-9-oxo-9H-indeno[2,1-b]pyridinium iodide; 2,2'-[1,4-phenylenebis(methylylidenenitrilo)]bis(5-methylphenol); 3-methyl-5-{[5-(2-nitrophenyl)-2-furyl]methylene}-2-thioxo-1,3-thiazolidin-4-one; 5-benzyl-2-methyl-2-(4-nitrophenyl)-2,3-dihydro-1,3,4-thiadiazole; 5-hydroxy-5-methyl-2-phenyl-3-isoxazolidinone; 2-(3-pyridinylmethylene)-1-benzothiophen-3(2H)-one; 2-imino-5-{[5-(2-nitrophenyl)-2-furyl]methylene}-1,3-thiazolidin-4-one; 4-tert-butyl-2-[(3-nitrobenzylidene)amino]phenol; [4-(difluoromethoxy)benzylidene](phenyl)azane oxide; and 1-[(4-nitrophenyl)sulfonyl]-1H-pyrrole.

In another embodiment of the present disclosure, a method for increasing the efficacy of a readthrough drug is provided. As described herein, readthrough drugs reduce the efficiency of translation termination at an in-frame PTC. The present methods increase the efficacy of readthrough drugs by, e.g., inhibiting NMD in a gene-specific manner, thereby providing increased levels of transcripts available for translation and suppression or readthrough of PTCs contained therein. Accordingly, the method comprises identifying an exon-exon junction that is downstream of a PTC in mRNA transcribed in a eukaryotic cell from a disease-causing nonsense mutant gene (e.g., as described herein) or a gene containing a naturally occurring PTC (e.g., as described herein). In some aspects the method involves identifying one or more exon-exon junctions with EJCs. The method further comprises introducing into the cell (e.g., and the nucleus of the cell) an ASO specific to a region of the mRNA upstream of the identified exon-exon junction(s), in sufficient quantity to inhibit deposition of EJC, inhibiting NMD of the mRNA, for example as described herein. The method further comprises introducing into the cell a composition (e.g., comprising a drug or compound provided herein) that promotes readthrough of the PTC introduced by the nonsense mutation. Typically, the composition is introduced in sufficient quantity, or in an effective amount, to result in greater readthrough of the PTC in the mRNA than would occur in the absence of the composition. Increasing readthrough of the PTC results in an increase of full-length protein as compared, for example, to levels of full-length protein in the absence of the composition (e.g., as described herein). In some aspects, the method is ameliorative or preventative of disease or condition, such as those provided herein, for example when the method is performed on cells in an individual, e.g., a human.

In another embodiment, methods of treating an individual having a disease or disorder caused by a nonsense mutation are provided. "Individual," as used herein, refers to an individual organism. In some aspects, "individual" may be used interchangeably with "subject," or "patient." In some embodiments, an individual is a mammal, for example, a human, a nonhuman primate, a mouse, a rat, a cat, a dog, a cattle, a goat, a pig, a sheep, or a plant. In some embodiments, the individual is a human having or at increased risk of having a disease or disorder caused by a nonsense mutation. If an individual is "at an increased risk" of having a disease or disorder caused by a nonsense mutation, the method involves preventative or prophylactic treatment. For example, an individual may be at an increased risk of having such a disease or disorder because of family history of the disease (e.g., the individual has a genetic predisposition). Many of the diseases and disorders described herein are primarily, if not entirely, genetic based diseases, e.g., β-thalassemia (nonsense mutations in HBB), Rett syndrome (nonsense mutations in MECP2), cystic fibrosis (nonsense mutations in CFTR), and Duchenne/Becker muscular dystrophy (nonsense mutations in DMD). Thus, in some aspects, an individual having one or more nonsense mutations in these genes (or others associated with diseases or disorder caused by nonsense mutations) but not yet diagnosed with such a disease or disorder, is an individual at increased risk of having a disease or disorder caused by a nonsense mutation. Typically, individuals at an increased risk of having such a disease or disorder benefit from prophylactic treatment (e.g., by preventing or delaying the onset or progression of the disease or disorder).

The method comprises administering to an individual a pharmaceutical composition (e.g., as described herein) comprising a therapeutically effective amount of an ASO that inhibits NMD of a PTC-containing mRNA expressed from a gene comprising a disease-causing nonsense mutation in the individual. Such genes that may comprise a disease-causing nonsense mutation include, but are not limited to, HBB, MECP2, CFTR, DMD and IDUA. Additional nonsense mutations can be found in the Human Gene Mutation Database (HGMD). Examples of specific alleles of these genes that comprise a nonsense mutation are provided in Table 1.

In some embodiments, the method comprises administering therapeutically effective amounts of provided pharmaceutical compositions to an individual having or at increased risk of having a disease or disorder selected from the following non-limiting list: Usher syndrome, ataxia telangiectasia, hemophilia A and B, Hailey-Hailey disease, Ullrich disease, methylmalonic academia, carnitine palmitoyltransferase 1A deficiency, peroxisome biogenesis disorders, limb girdle muscular dystrophy, Schmid metaphyseal chondrodysplasia, Sandhoff disease, Marfan syndrome, anemia, epidermolysis bullosa simplex, Tay-Sachs disease, triose phosphate isomerase deficiency, Alzheimer's disease, long-QT syndrome, insulin resistance, maple syrup urine disease, hereditary fructose intolerance, X-linked severe combined immunodeficiency, inherited cancers such as those due to BRCA1 nonsense mutations, carbohydrate metabolism disorders, amino acid metabolism disorders, lipoprotein metabolism disorders, lipid metabolism disorders, lysosomal enzymes metabolism disorders, steroid metabolism disorders, purine metabolism disorders, pyrimidine metabolism disorders, metal metabolism disorders, porphyrin metabolism disorders, and heme metabolism disorders.

One embodiment is a method of treating an individual having or at an increased risk of having β-thalassemia. The method comprises administering to the individual a pharmaceutical composition comprising a therapeutically effective amount of an (at least one, one or more) ASO that inhibits NMD of a PTC-containing mRNA expressed from an HBB allele in the individual. Examples of HBB alleles include, but are not limited to, those provided in Table 1 (e.g., CM810001, CM880039, CM034660, CM880040, and CM900122). In some embodiments, the ASO comprises a sequence selected from a sequence provided herein, for example SEQ ID NOs: 1-19. In some embodiments, the ASO comprises a sequence as embodied by SEQ ID NO:15 or SEQ ID NO:16. As used throughout this application, the term "an (at least one, one or more) ASO" means that all ASOs used are the same (e.g., all have the same sequence) and/or that a variety of ASOs (e.g., ASOs having two or more different sequences) is used.

In some embodiments, the method further comprises administering a therapeutically effective amount of one or more drugs that promotes the readthrough of PTCs, for example as described herein. In some embodiments, the one or more drug(s) is, an aminoglycoside, or salts, analogs, or derivatives thereof. An aminoglycoside(s) may be selected from the non-limiting group consisting of amikacin, arbekacin, gentamicin, kanamycin, neomycin, netilmicin, paromomycin, rhodostreptomycin, streptomycin, tobramycin, apramycin, G418 (geneticin), lividomycin, NB30, NB54, or NB84. In some embodiments, the one or more drug(s) is not an aminoglycoside. Examples of drugs that promote readthrough but are not aminoglycosides are known in the art and include, for example, negamycin, clitocine, acetylaminobenzoic acids such as 3-[2-(4-tertbutyl-phenoxy)-acetylamino]-benzoic acid and 3-{2-[4-(1,1-dimethylpropyl)-phenoxy]acetylamino}-benzoic acid, readthrough compound (RTC) #13, RTC #14, erythromycin, oleandomycin, tylosin, spiramycin, and josamycin. Salts, analogs, or derivatives of any of the aforementioned drugs may be used to practice the methods described herein. The drug that promotes readthrough of PTCs may be administered simultaneously, sequentially, or as part of the same pharmaceutical composition comprising the ASO(s). In some embodiments, the method further comprises administering a pharmaceutical composition (e.g., comprising a drug or compound provided herein) that inhibits NMD, for example as described herein.

One embodiment is a method of treating an individual having or at an increased risk of having Rett syndrome. The method comprises administering to the individual a pharmaceutical composition comprising a therapeutically effective amount of an ASO that inhibits NMD of a PTC-containing mRNA expressed from a MECP2 allele in the individual. Examples of MECP2 alleles include, but are not limited to, those provided in Table 1 (e.g., CM060329, CM023409, HM971529, CM010332, CM057720, CM010333, CM035705, CM055984, and CM076290). In some embodiments, the ASO comprises a sequence selected from a sequence provided herein, for example SEQ ID NOs: 20-38. In some embodiments, the ASO comprises a sequence selected from SEQ ID NO:29, SEQ ID NO:30, SEQ ID NO:31, or SEQ ID NO:32.

In some embodiments, the method further comprises administering a therapeutically effective amount of one or more drugs that promotes the readthrough of PTCs, for example as described and provided herein.

A further embodiment is a method of treating an individual having or at an increased risk of having cystic fibrosis and/or CBAVD. The method comprises administering to the individual a pharmaceutical composition comprising a therapeutically effective amount of an ASO that inhibits NMD of a PTC-containing mRNA expressed from a CFTR allele in the individual. Examples of CFTR alleles include, but are not limited to, those provided in Table 1 (e.g., CM960290, CM920186, CM993870, CM970297, CM900061, CM003260, CM993871, CM972963, CM920192, CM930137, CM900062, CM920194, CM024696, CM983581, CM983582, CM931253, and CM960291). In some embodiments, the ASO comprises a sequence selected from a sequence provided herein, for example SEQ ID NOs: 39-114.

In some embodiments, the method further comprises administering a therapeutically effective amount of one or more drugs that promotes the readthrough of PTCs, for example as described and provided herein.

A further embodiment is a method of treating an individual having or at an increased risk of having DMD/BMD. The method comprises administering to the individual a pharmaceutical composition comprising a therapeutically effective amount of an ASO that inhibits NMD of a PTC-containing mRNA expressed from a DMD allele in the individual. Examples of CFTR alleles include, but are not limited to, those provided in Table 1 (e.g., CM054661, CM960494, CM040028, CM084901, CM043277, CM950349, CM070908, and CM022961). In some embodiments, the ASO comprises a sequence selected from a sequence provided herein, for example SEQ ID NOs: 115-190.

In some embodiments, the method further comprises administering a therapeutically effective amount of one or more drugs that promotes the readthrough of PTCs, for example as described and provided herein.

Pharmaceutical Compositions

In some embodiments, pharmaceutical compositions comprising one or more ASO(s) and optionally one or more readthrough drug(s) are provided. In some aspects, the ASO(s) and additional drug(s) (drugs that are not ASOs specific to target regions bound by EJCs for the inhibition of NMD) are referred to as agents or active ingredients of the pharmaceutical compositions provided herein. The compositions comprising ASO(s) and optionally additional drug(s) can be mixed with a pharmaceutically acceptable carrier, either taken alone or in combination with the one or more additional therapeutic agents described above, to form pharmaceutical compositions. A pharmaceutically acceptable carrier is compatible with the active ingredient(s) of the composition (and preferably, capable of stabilizing it). Such compositions are delivered or administered in effective amounts to treat an individual, such as a human having a disease or disorder resulting from a nonsense mutation, for example those described herein. To "treat" a disease, means to reduce or eliminate a sign or symptom of the disease, to stabilize the disease, and/or to reduce or slow further progression of the disease. In some embodiments, "treat", "treatment" or "treating" is intended to include prophylaxis, amelioration, prevention or cure from the disease. For example, treatment of muscular dystrophies according to use of the compositions and methods provided herein may result in e.g., preventing or slowing of muscle degeneration, preventing or decreasing fatigue, increasing muscle strength, reducing blood levels of creatine kinase (CK), preventing or decreasing difficulty with motor skills, preventing or decreasing muscle fiber deformities, increasing cognition, preventing or improving epileptic symptoms (e.g., preventing or decreasing seizure activity; decreasing frequency of convulsions), improving eye function, restoring or preventing of eye abnormalities (e.g., retinal detachment), preventing or improving dystrophic abnormalities (e.g., as determined by muscle biopsy), reversing, reducing, or preventing cardiac dysfunction (resulting from, e.g., cardiomyopathy) manifested by e.g., congestive heart failure and arrhythmias, etc. Additionally, treatment of blood disorders such as anemia and β-thalassemia according to use of the compositions and methods provided herein may result in, for example, decreased or no anemia, decreased tiredness, decreased breathlessness, and increase of exercise tolerance, as determined by routine physical examination as well as pulse oximetry, hemoglobin electrophoresis; serum transferrin, ferritin, Fe binding capacity analysis; urine urobilin & urobilogen assays; peripheral blood smear test; hematocrit analysis; and serum bilirubin analysis. Treatment of cystic fibrosis according to use of the compositions and methods provided herein may result in, for example, increased mucociliary clearance and decreased inflammation and infection of the lungs, decreased pulmonary hypertension, decreased mucus in the paranasal sinuses, increased growth, increased food intake and weight gain, decreased shortness of breath, decreased bowel obstruction, and lack of infertility in males treated in utero. Treatment of Rett syndrome according to use of the compositions and methods provided herein may result in, for example with post-natal treatment in early development (e.g., in the first 18 months following birth, and thereafter), normal development of language and motor skills, little or no loss of purposeful hand use, little or no acquired deceleration in the rate of head growth, no or decreased breathing irregularities such as hyperventilation, breathholding, or sighing, and prevention of autistic like behaviors. In some aspects, treatment of those suffering from Rett syndrome at a later stage in life may result in increased cognition, increased communication, decreased stereotyped hand movements, decreased prevalence and/or duration of seizures, and decreased gastrointestinal disorders including constipation.

Actual dosage levels of active ingredients in the pharmaceutical compositions of the invention can be varied to obtain an amount of the active ASO and optionally other agent(s) that is effective to achieve the desired therapeutic response for a particular patient, combination, and mode of administration. The selected dosage level depends upon the activity of the particular ASO and other agent(s), the route of administration, the severity of the condition being treated, the condition, and prior medical history of the patient being treated. However, it is within the skill of one in the art to start doses of the compositions described herein at levels lower than required to achieve the desired therapeutic effort and to gradually increase the dosage until the desired effect is achieved. A "therapeutically effective amount," as used herein, refers to an amount of a compound and/or an additional therapeutic agent, or a composition thereof that results in improvement (complete or partial) of a disease or disorder caused by a nonsense mutation, e.g., reduction (partial or complete) of severity and/or duration of the condition. A therapeutically effective amount also refers to an amount that prevents or delays the onset of a disease or disorder caused by a nonsense mutation. The therapeutically effective amount will vary with the particular condition being treated, the age and physical condition of the subject being treated, the severity of the condition, the duration of the treatment, the nature of the concurrent therapy (if any), the specific route of administration, and like factors are within the knowledge and expertise of the health practitioner. For example, an effective amount can depend upon the duration the subject has had the disease. In some aspects, an effective amount of a composition described herein when administered to a subject results in e.g., increased muscle strength, increased motility, restoration of muscle function or phenotype, decreased fatigue, decreased difficulty with motor skills, decreased anemia, decreased epileptic symptoms, etc. In some aspects, the desired therapeutic or clinical effect resulting from administration of an effective amount of a composition described herein, may be measured or monitored by methods known to those of ordinary skill in the art. e.g., by routine physical examination, monitoring the creatine kinase (CK) levels in a subject's blood, by electromyography, by electroencephalography (EEG), by pulse oximetry, and/or by histological examination of a muscle biopsy.

In the combination therapies, an effective amount can refer to each individual agent or to the combination as a whole, wherein the amounts of all agents administered are together effective, but wherein the component agent of the combination may not be present individually in an effective amount.

The pharmaceutical compositions described herein (e.g., those containing ASOs and optionally readthrough drugs), can be administered to a subject by any suitable route. ASOs and readthrough drugs can be administered simultaneously or sequentially. If the ASOs and readthrough drugs are administered simultaneously they can be administered in a single composition or different compositions. For example, the ASOs may be administered in a first composition (e.g., intravenously) and the readthrough drugs maybe administered in a secon composition (e.g., orally). If the ASOs and the readthrough drugs are administered separately, it is only necessary that they be administered sufficiently close in time to have the desired effect (e.g., enhanced protein production). For example, compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, intravitreal, retrobulbar, intrapulmonary, intrathecal, subcutaneous and intraarticular injection and infusion. Surgical implantation also is contemplated, including, for example, embedding a composition of the disclosure in the body such as, for example, in the brain, in the abdominal cavity, under the splenic capsule, brain, or in the cornea.

The pharmaceutical compositions described herein can also be administered in the form of liposomes. As is known in the art, liposomes generally are derived from phospholipids or other lipid substances. Liposomes are formed by mono- or multi-lamellar hydrated liquid crystals that are dispersed in an aqueous medium. Any nontoxic, physiologically acceptable, and metabolizable lipid capable of forming liposomes can be used. The present compositions in liposome form can contain, in addition to an agent of the present disclosure, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33, et seq.

Dosage forms for topical administration of the pharmaceutical compositions described herein include powders, sprays, ointments, and inhalants as described herein. The active agent(s) is mixed under sterile conditions with a pharmaceutically acceptable carrier and any needed preservatives, buffers, or propellants which may be required. Ophthalmic formulations, eye ointments, powders, and solutions also are contemplated as being within the scope of this disclosure.

Pharmaceutical compositions (e.g., those containing ASOs and optionally readthrough drugs) for parenteral injection comprise pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and non-aqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

Compositions also can contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the pharmaceutical compositions described herein (e.g., those containing ASOs and optionally readthrough drugs), it is desirable to slow the absorption of the drug from subcutaneous or intramuscular injection. This result can be accomplished by the use of a liquid suspension of crystalline or amorphous materials with poor water solubility. The rate of absorption of the active agent(s) then depends upon its rate of dissolution which, in turn, may depend upon crystal size and crystalline form. Alternatively, delayed absorption of a parenterally administered active agent(s) is accomplished by dissolving or suspending the agent(s) in an oil vehicle.

Injectable depot forms are made by forming microencapsule matrices of the agent(s) (e.g., ASOs, readthrough drugs) in biodegradable polymers such a polylactide-polyglycolide. Depending upon the ratio of agent(s) to polymer and the nature of the particular polymer employed, the rate of agent(s) release can be controlled. Examples of other biodegradable polymers include poly(orthoesters) and poly (anhydrides). Depot injectable formulations also are prepared by entrapping the agent(s) in liposomes or microemulsions which are compatible with body tissue.

The injectable formulations can be sterilized, for example, by filtration through a bacterial- or viral-retaining filter, or by incorporating sterilizing agents in the form of sterile solid compositions which can be dissolved or dispersed in sterile water or other sterile injectable medium just prior to use.

Also described here are methods for oral administration of the pharmaceutical compositions described herein. Oral solid dosage forms are described generally in Remington's Pharmaceutical Sciences, 18th Ed., 1990 (Mack Publishing Co. Easton Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556). In general, the formulation includes the agent(s) (e.g., ASOs and optionally readthrough drugs) and inert ingredients which protect against degradation in the stomach and which permit release of the biologically active material in the intestine.

In such solid dosage forms, the agent(s) is mixed with, or chemically modified to include, a least one inert, pharmaceutically acceptable excipient or carrier. The excipient or carrier preferably may permit uptake into the blood stream from the stomach or intestine. In a most preferred embodiment, the excipient or carrier increases uptake of the agent(s), overall stability of the agent(s) and/or circulation time of the agent(s) in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO®, EMDEX®, STA-RX 1500®, EMCOMPRESS® and AVI-CEL®, (b) binders such as, for example, methylcellulose ethylcellulose, hydroxypropyhnethyl cellulose, carboxymethylcellulose, gums (e.g., alginates, acacia), gelatin, polyvinylpyrrolidone, and sucrose, (c) humectants, such as glycerol, (d) disintegrating agents, such as agar-agar, calcium carbonate, potato or tapioca starch, alginic acid, certain silicates, sodium carbonate, starch including the commercial disintegrant based on starch, EXPLOTAB®, sodium starch glycolate, AMBERLITE®, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffin, (f) absorption accelerators, such as quaternary ammonium compounds and fatty acids including oleic acid, linoleic acid, and linolenic acid (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay, (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX® 4000, CARBO-WAX® 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

Solid compositions of a similar type also can be employed as fillers in soft and hard-filled gelatin capsules, using such excipients as lactose or milk sugar, as well as high molecular weight polyethylene glycols and the like.

The solid dosage forms of tablets, dragees, capsules, pills, and granules can be prepared with coatings and shells, such as enteric coatings and other coatings well known in the pharmaceutical formulating art. They optionally can contain opacifying agents and also can be of a composition that they release the active ingredients(s) only, or preferentially, in a part of the intestinal tract, optionally, in a delayed manner. Exemplary materials include polymers having pH sensitive solubility, such as the materials available as EUDRAGIT® Examples of embedding compositions which can be used include polymeric substances and waxes.

The agent(s) also can be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the agents(s) (e.g., ASOs and optionally readthrough drugs), the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydroflirfuryl alcohol, polyethylene glycols, fatty acid esters of sorbitan, and mixtures thereof.

Besides inert diluents, the oral compositions also can include adjuvants, such as wetting agents, emulsifying and suspending agents, sweetening, coloring, flavoring, and perfuming agents. Oral compositions can be formulated and further contain an edible product, such as a beverage. Oral composition can also be administered by oral gavage.

Suspensions, in addition to the active ingredient(s), can contain suspending agents such as, for example ethoxylated isostearyl alcohols, polyoxyethylene sorbitol and sorbitan esters, microcrystalline cellulose, aluminum metahydroxide, bentonite, agar-agar, tragacanth, and mixtures thereof.

Also contemplated herein is pulmonary delivery of the ASOs and optionally readthrough drugs. The agents are delivered to the lungs of a mammal while inhaling, thereby promoting the traversal of the lung epithelial lining to the blood stream. See, Adjei et al., Pharmaceutical Research 7:565-569 (1990); Adjei et al., International Journal of Pharmaceutics 63:135-144 (1990) (leuprolide acetate); Braquet et al., Journal of Cardiovascular Pharmacology 13 (suppl. 5): s. 143-146 (1989)(endothelin-1); Hubbard et al., Annals of Internal Medicine 3:206-212 (1989)($\alpha$1-antitrypsin); Smith et al., J. Clin. Invest. 84:1145-1146 (1989) ($\alpha$1-proteinase); Oswein et al., "Aerosolization of Proteins," Proceedings of Symposium on Respiratory Drug Delivery II, Keystone, Colo., March, 1990 (recombinant human growth hormone); Debs et al., The Journal of Immunology 140:3482-3488 (1988) (interferon-$\gamma$ and tumor necrosis factor $\alpha$) and Platz et al., U.S. Pat. No. 5,284,656 (granulocyte colony stimulating factor).

Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art.

Some specific examples of commercially available devices suitable for the practice of the invention are the ULTRAVENT® nebulizer, manufactured by Mallinckrodt, Inc., St. Louis, Mo.; the ACORN II® nebulizer, manufactured by Marquest Medical Products, Englewood, Colo.; the VENTOL® metered dose inhaler, manufactured by Glaxo Inc., Research Triangle Park, N.C.; and the SPINHALER® powder inhaler, manufactured by Fisons Corp., Bedford, Mass.

All such devices require the use of formulations suitable for the dispensing of the agent(s) described herein. Typically, each formulation is specific to the type of device employed and can involve the use of an appropriate propellant material, in addition to diluents, adjuvants, and/or carriers useful in therapy.

The composition is prepared in particulate form, preferably with an average particle size of less than 10 μm, and most preferably 0.5 to 5 μm, for most effective delivery to the distal lung.

Carriers include carbohydrates such as trehalose, mannitol, xylitol, sucrose, lactose, and sorbitol. Other ingredients for use in formulations may include lipids, such as DPPC, DOPE, DSPC and DOPC, natural or synthetic surfactants, polyethylene glycol (even apart from its use in derivatizing the inhibitor itself), dextrans, such as cyclodextran, bile salts, and other related enhancers, cellulose and cellulose derivatives, and amino acids.

Also, the use of liposomes, microcapsules or microspheres, inclusion complexes, or other types of carriers is contemplated.

Formulations suitable for use with a nebulizer, either jet or ultrasonic, typically comprise an agent of the invention dissolved in water. The concentration of ASOs varies and ranges, for example, from about 0.1 to about 25 mg per mL of solution. The formulation also can include a buffer and a simple sugar (e.g., for protein stabilization and regulation of osmotic pressure). The nebulizer formulation also can contain a surfactant to reduce or prevent surface-induced aggregation of the inhibitor composition caused by atomization of the solution in forming the aerosol.

Formulations for use with a metered-dose inhaler device generally comprise a finely divided powder containing the agent suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid also can be useful as a surfactant.

Formulations for dispensing from a powder inhaler device comprise a finely divided dry powder containing the agent(s) and also can include a bulking agent, such as lactose, sorbitol, sucrose, mannitol, trehalose, or xylitol, in amounts which facilitate dispersal of the powder from the device, e.g., 50 to 90% by weight of the formulation.

Nasal delivery of the agent(s) and compositions of the invention also are contemplated. Nasal delivery allows the passage of the agent(s) or composition to the blood stream directly after administering the therapeutic product to the nose, without the necessity for deposition of the product in the lung. Formulations for nasal delivery include those with dextran or cyclodextran. Delivery via transport across other mucous membranes also is contemplated.

Compositions for rectal or vaginal administration are preferably suppositories which can be prepared by mixing the agent(s) with suitable nonirritating excipients or carriers, such as cocoa butter, polyethylene glycol, or suppository wax, which are solid at room temperature, but liquid at body temperature, and therefore melt in the rectum or vaginal cavity and release the active agent.

In order to facilitate delivery of agent(s) across cell and/or nuclear membranes, compositions of relatively high hydrophobicity are preferred. Agent(s) can be modified in a manner which increases hydrophobicity, or the agents can be encapsulated in hydrophobic carriers or solutions which result in increased hydrophobicity.

In one aspect, the invention provides kits comprising a pharmaceutical composition comprising a therapeutically effective amount of one or more ASO and a therapeutically effective amount of one or more readthrough drugs and instructions for administration of the pharmaceutical composition. In some aspects of the invention, the kit can include a pharmaceutical preparation vial, a pharmaceutical preparation diluent vial, and the ASO(s) and additional agent(s). The diluent vial contains a diluent such as physiological saline for diluting what could be a concentrated solution or lyophilized powder of the agent of the invention. In some embodiments, the instructions include instructions for mixing a particular amount of the diluent with a particular amount of the concentrated pharmaceutical preparation, whereby a final formulation for injection or infusion is prepared. In some embodiments, the instructions include instructions for use in a syringe or other administration device. In some embodiments, the instructions include instructions for treating a patient with an effective amount of the ASO(s) and optional additional agent(s). It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

EXAMPLES

The present invention will be more specifically illustrated by the following Examples. However, it should be understood that the present invention is not limited by these examples in any manner.

Example 1: Identification of EJC-Bound Exon-Exon Junctions Located Downstream of Nonsense Mutations Rationale Although it is known that EJCs are deposited immediately upstream of approximately 70% every exon-exon junction in each gene (24, 25), it is paramount to determine which exon-exon junctions should be targeted by ASOs in order to prevent EJC deposition. Using RNase H protection assays, EJC-protected areas were mapped in vitro, exclusively to a region between −20 to −24 nt upstream of the 3' end of test exons (23).

Through RNA immunoprecipitation and PCR amplification of sequences immediately surrounding this region, EJC-bound exon-exon junctions are identified in vivo, in the context of RTT, CFTR, HBB, DMD, and IDUA genes.

Disease-Associated Minigenes

Given the lack of cell lines with the mutant alleles listed in Table 1, with the exception of CFTR-W1282X (Coriell GM03401 and IB3 cells) and the IDUA-W402X mutations the experiments are carried out using minigenes transfected into HeLa, U2OS, HEK293 cells among others or integrated into U2OS cells' (as described in Hossain M, Stillman B, 2012, Meier-Gorlin syndrome mutations disrupt an Orc1 CDK inhibitory domain and cause centrosome reduplications. *Genes & Development* 26: 1797-810. The minigenes are constructed in a frame-preserving manner, including an initiation codon, with all internal exons flanked by up to 300 nt of intronic sequences, as follows: RTT minigene includes all exons from isoform 1 (2-4); CFTR minigene includes exons 22-27; HBB minigene includes all exons (1-3); DMD minigene includes exons 73-78 and IDUA minigene includes exons 8-14. As EJCs can play a role in mRNA export (26), the presence of at least one EJC upstream of the mutations to be tested ensures export of transcripts to the cytoplasm, even when the deposition of downstream EJCs is deliberately blocked. Minigenes that are integrated into U2OS cell are flanked by GFP-expressing cDNA (5'end) and T7 sequence (3'end) to determine protein levels. The integration process is as follows: transgenes driven from a hybrid cytomegalovirus (CMV) immediate early promoter, that was repressed by a tetracycline-regulated repressor protein, are stably integrated into a U2OS cell line that harbors a single FRT integration site, giving rise to isogenic cell lines expressing either wild-type of PTC-harboring transgenes (HBB, CFTR or MECP2).

RNA Immunoprecipitation (RIP)

Figure 2:
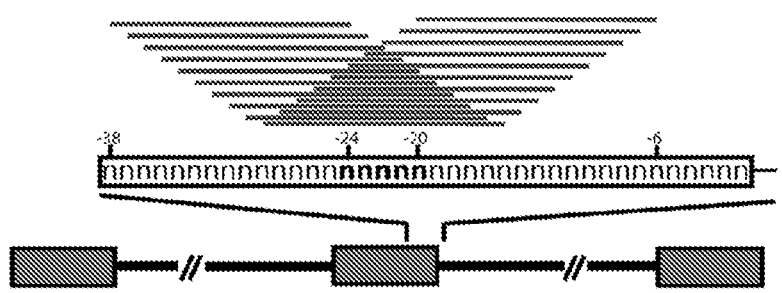
FIG. 2 is a schematic representation of the ASO microwalk targeting the EJC deposition region. Blue lines at the top of the figure denote 15-mer ASOs shifted by 1 nt, covering a region of 33 nt from −6 to −38.

To isolate EJC-bound RNA regions, a slightly modified version of RIP (27) is performed in combination with micrococcal nuclease (MNase) digestion (28, 29) (FIG. 1). For the purposes of the instant approach, endogenous or T7-tagged eIF4A3 (the anchor protein of the EJC), is immunoprecipitated (IP) from lysates of HeLa cells expressing the above minigenes. Briefly, HeLa cells are co-transfected with one of the four minigenes and either an empty vector (pCGT7) or one expressing T7-eIF4A3. Forty-three hours later, cells are treated with cycloheximide for five hours to block the pioneer round of translation, in order to preserve EJCs on the transcripts (25). At first, no crosslinking prior to harvesting the cells is used, as this step reduces the efficiency of RNA recovery. However, if the protocol results in low RNA co-IP efficiency, due to weak eIF4A3-RNA interactions, UV crosslinking is performed prior to harvesting the cells (26). After cycloheximide treatment, cells are lysed in 0.2% NP-40 and 200 mM NaCl. Lysates are incubated with Dynabeads coupled with antibody specific to either eIF4A3 or T7. After mRNP complexes are IPed, unprotected RNA regions are digested with MNase in the presence of 5 mM $CaCl_2$ (FIG. 2). The digestion time and concentration of MNase is optimized to generate fragments of approximately 60-70 nt in length. Protected RNA regions bound to eIF4A3 are pulled down using magnets and unprotected, free regions are washed out. As a control, undigested IPs are generated as well (see below) (FIG. 1). RNA is subsequently extracted from the beads using Trizol.

RT-PCR Amplification of Immunoprecipitated Regions

To identify exon-exon junctions that co-IP with eIF4A3, a 60-nt window spanning each of the exon-exon junctions in the four minigenes is PCR-amplified (FIG. 1). Briefly, cDNA synthesis using random primers is first performed, followed by radioactive-PCR amplification of a region spanning 50 nt of the 3' end of one exon and 10 nt of the 5' end of the adjacent exon (FIG. 1). Amplification of a product encompassing the junction ensures the identification of EJC-protected regions that resulted from splicing. Moreover, to ensure that the MNase digestion is efficient and that the binding of EJCs to mRNAs specifically at exon-exon junctions is detected, PCR amplification of a region of the same size is performed, which is not expected to be EJC-bound, in the last exon of each transcript ("control region") (FIG. 1). If all the conditions work properly, amplification of this product is not expected in MNase-treated samples, whereas it will likely be present in the undigested control. In contrast, the PCR products corresponding to the exon-exon junctions should be observed in both MNase-treated and untreated IP samples. To assess the enrichment of exon-exon junctions among EJC-protected areas, the ratio of MNase-treated over untreated PCR products for each fragment (exon-exon junctions or random regions) is calculated. While a ratio that approaches 0 for the "control regions" is expected, the products corresponding to exon-exon junctions should result in a ratio that approaches 1.

The above methodology confirms that potential exon-exon junctions to be targeted by ASOs to abrogate NMD have EJCs bound upstream. In addition, these results will shed light on the question of whether all exon-exon junctions are bound by EJCs in vivo.

Example 2: Identification of ASOs that Target EJC-Bound Regions to Abrogate NMD Rationale As evidence suggests that transcript degradation competes against translational readthrough, abolishing NMD increases the efficacy of readthrough drugs (5, 6). There are several known ways in which NMD can be inhibited; however all of them affect NMD globally, and a subset also affect important cellular processes (e.g., translation, PI3K signaling).

Accordingly, this work provides a tool to abrogate NMD in a gene-specific manner, so that it can be used safely in patients. Given that the EJC is a key landmark that distinguishes a PTC from a normal termination signal, if the deposition of EJCs were to be blocked, no landmark would be present on the mRNA to highlight the occurrence of a PTC. In this scenario, a PTC would tend to be treated as a normal termination signal, and NMD would not be triggered. Thus, as demonstrated herein, ASOs directed against a region where EJCs are expected to bind prevent EJC deposition, reminiscent of how splicing can be altered by blocking splicing-factor binding sites using ASOs (7-10). As minimizing potential unwanted effects on splicing is desired, ASOs are tested that are 15 nt in length, at least initially, to cover a relatively small region, while retaining sufficient binding specificity. ASOs are typically designed to target at least the −20 to −24 region previously reported to be protected by the EJC (FIG. 2) (23). Blocking NMD deposition is a new application for ASOs, so in addition to uniform MOE phosphorothioate-modified ASOs (e.g., as described herein), other chemistries, e.g., morpholino or 2'O Me ASOs (from Gene Tools, Philomath, Oreg.), are tested as well, to compare their effectiveness.

Assessment of the Level of NMD for Each Disease Mutation

Before targeting EJC-protected exon-exon junctions with ASOs, the level of NMD for a subset of the mutations listed in Table 1 is assessed. In some examples, it is desirable to start with mutations located in the last presumptive EJC-bound exon, as targeting only one junction at a time will simplify the interpretation of results. Once the effectiveness of preventing EJC deposition by ASOs is confirmed, two or more junctions are targeted. In some examples, three mutations for each gene are selected, and only mutations that lead to a transcript level <50% of the wild-type transcript will be targeted by the ASO microwalk (discussed below). If any of the selected mutations does not fulfill this criterion, a new one from the list is selected. Briefly, minigenes carrying the selected mutations and their wild-type versions are co-transfected with a GFP-expressing vector into HeLa cells. Forty-eight hours later, RNA is extracted and radioactive RT-PCR is performed. Products corresponding to the wild-type and mutant minigenes are normalized to GFP expression, and the percentage of the mutant over the wild-type transcript is calculated. In the case of integrated minigenes into U2OS cells, wild-type and mutant minigene products are normalized to endogenous housekeeping genes, e.g. GAPDH.

ASO Microwalk

Figure 3:
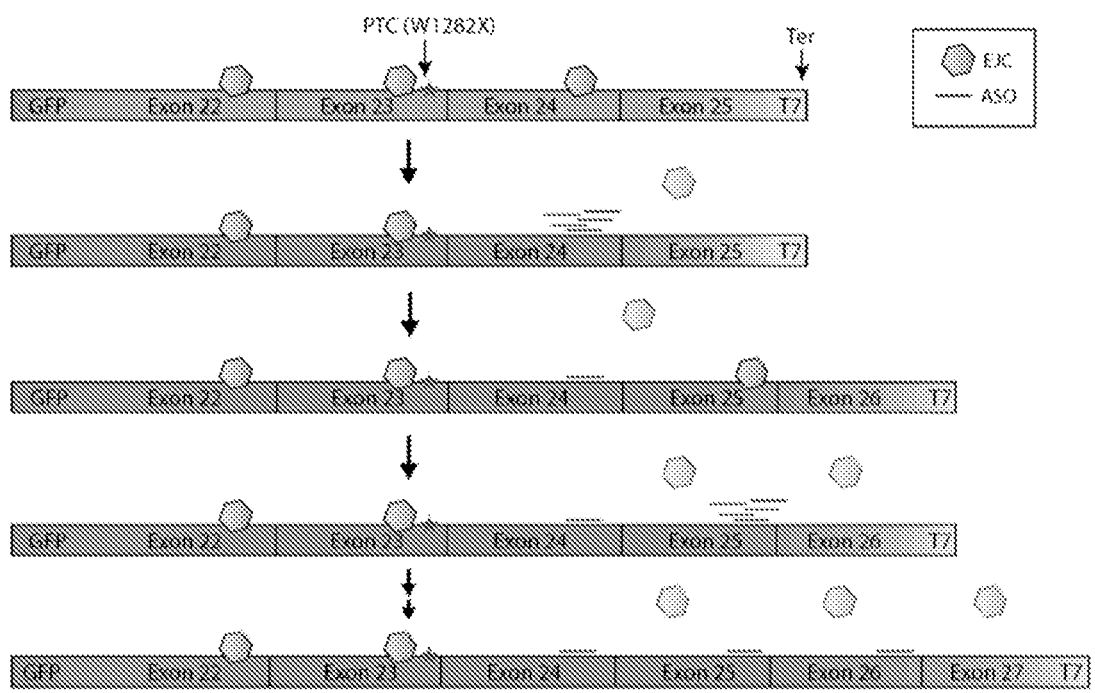
FIG. 3 is a schematic representation of the strategy for ASO microwalk targeting multiple exon-exon junctions.

ASO microwalks are performed as previously described (7), altogether targeting a region that spans 33 nt from −6 to −38 of the 3' end of exons that are EJC-bound (FIG. 2). Briefly, cell lines expressing minigenes carrying mutations in the last EJC-bound exon or their wild-type versions and GFP (by transfection using lipofectamine or induction with tetracycline) are co-transfected with each of the 15-mer ASOs, independently. In total, 19 ASOs that are consecutively shifted by 1 nt are tested for each EJC-bound exon-exon junction downstream of the mutations (FIG. 2). This methodology was followed in designing the sequences for the ASOs to target PTC-containing (e.g., disease-causing nonsense mutation) HBB alleles (See SEQ ID NOs 1-19), MECP2 alleles (See SEQ ID NOs 20-38), CFTR alleles (See SEQ ID NOs 39-114), DMD alleles (See SEQ ID NOs 115-190), and IDUA alleles (See SEQ ID Nos 191-268). Different concentrations of ASOs are tested to obtain a dose-response curve. In the case of genes containing more than one exon-exon junction downstream of a PTC, minigene intermediates are constructed to screen for NMD-inhibiting ASOs one junction at a time and in combination with the best targeting ASO that resulted from the screening of the upstream junction. A schematic representation of the method is shown in FIG. 3. Abrogation of NMD is assessed by RT-PCR, and the percentage of mutant transcript is calculated as described above. Because some of the ASOs might interfere with splicing-factor binding sites, it is important to determine whether the splicing of the targeted exons is adversely affected. Only the ASOs that abrogate NMD without negative effects on splicing are pursued.

RIP to Assess ASO-Mediated EJC-Blockage

RIP is used to determine whether the ASOs that inhibit NMD actually block EJC deposition. Briefly, RIP is performed as described above, but using lysates of HeLa cells that are also co-transfected with the best NMD-inhibiting ASOs for each minigene. If an ASO blocks EJC deposition, exon-exon junctions that were previously found to be EJC-bound should no longer co-IP with eIF4A3.

This example provides key experiments that allow the design and determination of ASOs that can be applied to targeting EJC deposition. The methodology thus identifies ASOs that abrogate NMD in a gene-specific manner, which not only can be applied to potentiate readthrough drugs and increase levels of functional truncated proteins, but will also provide a method to study EJC deposition and NMD mechanisms. Using known methods, ASOs may be tested for off-target effects and/or toxicity.

Example 3: Combining NMD-Inhibiting ASOs with Readthrough Drugs to Suppress Nonsense Mutations Rationale Studies have shown significant variability in the response to ataluren (2, 18), a readthrough drug that is currently in phase III clinical trials for cystic fibrosis (18). This variability is often observed in patients that carry the same mutation (e.g., CFTR W1282X) (2, 18). In some cases, patients with certain mutations show no response to ataluren (e.g., CFTR Q1313X) (18). In addition to patients with cystic fibrosis, DMD patients with nonsense mutations have also participated in studies using ataluren as a readthrough drug (3, 17). Moreover, other readthrough drugs have been tested for β-thalassemia and Rett syndrome, among other diseases, using cell lines from patients (6, 19, 20). Thus far, the treatment with ataluren has proven safe for patients, and holds promise to improve patients' lives. However, a way to inhibit NMD in patients, without adverse effects, would greatly enhance the effectiveness of drugs like ataluren. In this regard, the MOE phosphorothioate ASO chemistry has proven safe in animal studies and clinical trials performed to date (21). Therefore, the gene-specific approach to abrogate NMD described herein is expected to be beneficial to patients with nonsense alleles for a wide variety of genetic diseases, e.g., those provided herein.

Construction of a Reporter for the Assessment of Readthrough

Given the lack of cell lines expressing most of the mutant alleles addressed in this disclosure, reporters are constructed to assess the effectiveness of the combined ASO+ readthrough treatment. Briefly, the cDNA sequence of GFP is placed in-frame, upstream of each minigene and the T7 sequence is placed downstream of each minigene (e.g., as described herein). The natural translational termination signal of each minigene is removed and placed at the end of T7. GFP enables the detection of subtle changes in intensity that correlate with protein expression/concentration (30-32). Moreover, using an antibody specific to GFP, it has been shown that GFP detection can be precise enough to assess the stoichiometry of proteins that form a complex (30). A combination of FACS analysis and western blotting with near-infrared fluorescent imaging of IRDye-coupled antibodies (LI-COR) is thus used to measure differences in readthrough efficiency upon ASO treatment.

Combination of ASO and Readthrough Treatments

Using the minigene reporters described above, a combination of the best NMD-inhibiting ASOs and ataluren is tested. Briefly, the minigene reporters carrying nonsense mutations and the respective wild-type versions are co-transfected into HeLa cells with the targeting ASOs for 48 hours. Sixteen hours prior to harvesting, cells are treated with ataluren or DMSO (solvent) as a control, as previously described (1). Ataluren is obtained from Selleck Chemicals (Houston, Tex.), and typically used at 5 µg/ml (1), as well as comparing a range of concentrations. Cells are then lysed in RIPA buffer, and western blotting is performed to detect GFP expression. These results are compared to control-ASO-treated cells expressing the minigene reporters and treated with ataluren, as well as to cells treated with test or control ASO, but without ataluren. A control ASO can be one of the ASOs that do not block EJC deposition in the microwalk, an ASO to another irrelevant sequence, or an ASO containing several mismatches or scrambled sequence, compared to the lead ASO. An increase in GFP production is expected when cells are treated with targeting ASOs, compared to ASO-control-treated cells. To confirm that blocking NMD causes an increase in GFP production after ataluren treatment, a control experiment using a short-interfering RNA against UPF1 is performed. In addition, the western blot results are validated by analyzing cells from duplicate experiments using FACS (e.g., LSRII Cell Analyzer, Becton Dickinson, Franklin Lakes, N.J.) analysis of GFP expression.

The methodology of Example 4 allows the determination of which ASO in a particular disease paradigm is beneficial as a potentiating agent for ataluren. Abrogation of NMD will likely eliminate the variability observed in response to ataluren among cells carrying the same mutation, and ultimately in patients. Additionally, NMD-inhibiting ASOs may be tested in transgenic-mouse models carrying human genes with nonsense mutations. As MOE ASOs have been safely used in mice and nonhuman primates, and are currently in phase I-III clinical trials for various diseases (16), NMD-inhibiting ASOs are expected to be equally safe and effective.

Example 5: Inhibition of NMD by ASOs Targeting an HBB, MECP2, or CFTR Allele Containing a Disease-Causing Nonsense Mutation Materials and Methods A set of 19 overlapping 2'-O-methoxyethyl phosphorothioate (MOE-P=S) ASO 15mers targeting the canonical EJC region in exon 2 of HBB were synthesized. These were individually co-transfected at an initial concentration of 50 nM using Lipofectamine 2000 into HeLa cells with an HBB gene harboring a nonsense mutation in codon 39 in exon 2 (Q39X), which triggers NMD. The levels of spliced HBB mRNA were then measured after transient or induced expression using radioactive RT-PCR. Together, the overlapping ASOs span from −38 to −6 from the exon2/exon 3 junction. Truncated protein levels resulting from the ASO treatment were assessed by western blot analysis using anti-GFP antibody.

In parallel, a minigene reporter was generated consisting of MECP2 exons 2, 3 and 4 carrying the S65X mutation in exon 3, as well as its respective wild-type version. As described above, 19 15-mer ASOs were obtained that target a region spanning nucleotides −38 to −6 of the exon 3/4 boundary, and these ASOs were transfected individually in cells expressing the MECP2 mutant reporter or wild-type reporter.

Moreover, minigenes consisting of CFTR exons 22-25, 22-26 and 22-27 carrying the W1282X mutation in exon 23 as well as its restive wild-type version were generated. As described above, 19 15-mer ASOs were obtained that target a region spanning nucleotides −38 to −6 of the exons 24/25 boundary and transfected to CFTR minigene expressing cells. Once this screening identified the best NMD inhibiting ASO, it is then transfected in combination with each the 19 15-mer ASOs that target a region spanning nucleotides −38 to −6 of the exons 25/26 boundary. The resulting best combination of ASOs (from each exon-exon boundary) was then transfected in combination with each of the 19 15-mer ASOs that target a region spanning nucleotides −38 to −6 of the exons 26/27 boundary. The levels of spliced CFTR mRNA were then measured after induced expression using radioactive RT-PCR.

Results

Figure 4:
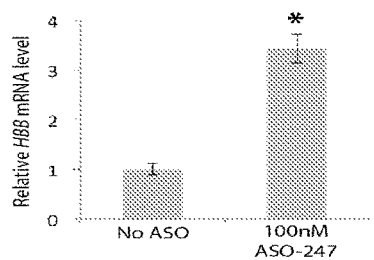
FIG. 4A is a table showing the results from radioactive RT-PCR of HeLa cells co-transfected with HBB reporters and ASOs, demonstrating an increase in mRNA levels of a PTC-containing HBB transcript (T39) resulting from inhibition of NMD by ASO247 (SEQ ID NO: 15) and ASO248 (SEQ ID NO: 16). Percentages of transcripts were normalized to WT.
FIG. 4B is a graph demonstrating the fold increase achieved by the most potent ASO targeting HBB exon 2 (247, SEQ ID NO: 15) in U2OS cells expressing HBB Q39X transcript, n=at least 3.
FIG. 4C is table showing the results of a western blot probed with anti-GFP antibody. The fold increase in truncated protein level corresponding to the ASO (247, SEQ ID NO: 15)-treated Q39X transcript.

Several ASOs inhibited inclusion of HBB exon 2, generating an abnormal mRNA, and little or no correctly spliced mRNA. Others had no effect, whereas three consecutive ASOs resulted in higher mRNA levels than the control-ASO (FIG. 4A). These ASOs had no effect on the level of the WT mRNA, consistent with a specific effect on the nonsense-mutant mRNA. Subsequently, the most potent ASO was transfected into U2OS cells expressing GFP-HBB-T7 integrated minigene carrying the Q39X allele. A 3.5-fold increase of the ASO-treated Q39X transcript was observed compared to untreated transcript level (FIG. 4B). Moreover, western blot analysis using anti-GFP antibody detected a 6-fold increase in truncated protein levels resulting from the ASO-treated Q39X transcript compared to untreated transcript (FIG. 4C).

Figure 5:
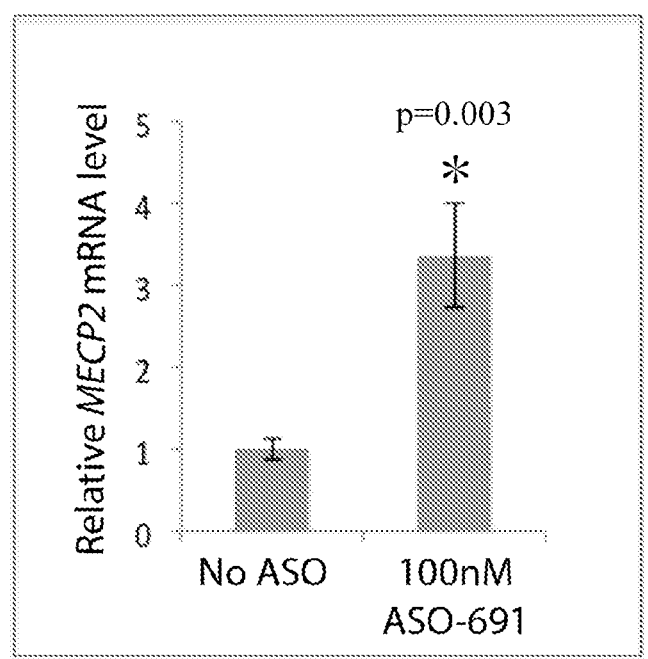
FIG. 5 is a graph demonstrating the fold increase achieved by the most potent ASO targeting MECP2 exon 3 (291, SEQ ID NO: 25) in U2OS cells expressing MECP2 S65X transcript, n=at least 3.

The results of independent transfection experiments showed that the majority of the ASOs had no effect on MECP2 mRNA level or splicing efficiency. However, a distinct cluster of ASOs significantly increased the MECP2 S65X mRNA level (FIG. 5A). The best targeting ASO increased MECP2 S65X mRNA level by approximately 3.5 fold compared to untreated control (FIG. 5B). As expected, no effect was observed on the WT mRNA, indicating that the effect is PTC-dependent.

Figure 6A:
FIG. 6A is a table showing the results from radioactive RT-PCR of cells transfected with most potent ASOs targeting CRTR junctions in combination, demonstrating an increase in mRNA levels of a PTC-containing CFTR transcript (W1282X) resulting from inhibition of NMD. Percentages of transcripts were normalized to untreated PTC-containing transcript.
Figure 6B:
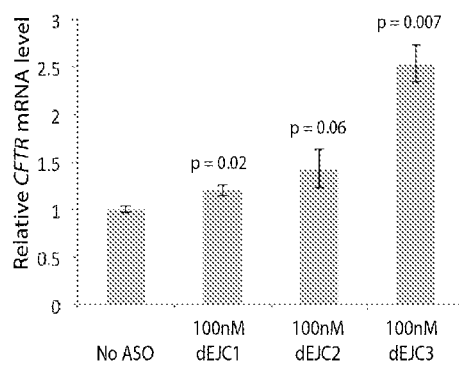
FIG. 6B is a graph corresponding to results from radioactive RT-PCR of cells expressing CFTR 22-17 minigene transfected with the most potent ASOs targeting each exon-exon junction downstream of the W1282X mutation independently (SEQ ID NO: 65, SEQ ID NO: 83, and SEQ ID NO: 107, respectively). ASO (SEQ ID NO: 107), which targets the last exon-exon junction is the most potent ASO.
Figure 6B:

Screening of ASOs for each of the boundaries downstream of the CFTR-W1282X resulted in the identification of three best targeting ASO that were tested in combination (FIG. 6A) or independently (FIG. 6B). RT-PCR results show that unexpectedly, targeting the last exon-exon junction of CFTR (26/27) has a more pronounced effect than targeting all three junctions at the same time. This observation could suggest that the last exon-exon junction in the CFTR gene is the most important one to mark the transcript for NMD.

REFERENCES

1. Welch E M, Barton E R, Zhuo J, Tomizawa Y, Friesen W J, Trifillis P, Paushkin S, Patel M, Trotta C R, Hwang S, Wilde R G, Karp G, Takasugi J, Chen G, Jones S, Ren H, Moon Y C, Corson D, Turpoff A A, Campbell J A, Conn M M, Khan A, Almstead N G, Hedrick J, Mollin A, Risher N, Weetall M, Yeh S, Branstrom A A, Colacino J M, Babiak J, Ju W D, Hirawat S, Northcutt V J, Miller L L, Spatrick P, He F, Kawana M, Feng H, Jacobson A, Peltz S W, Sweeney H L. PTC124 targets genetic disorders caused by nonsense mutations. *Nature* 2007; 447:87-91
2. Kerem E, Hirawat S, Armoni S, Yaakov Y, Shoseyov D, Cohen M, Nissim-Rafinia M, Blau H, Rivlin J, Aviram M, Elfring G L, Northcutt V J, Miller L L, Kerem B, Wilschanski M. Effectiveness of PTC124 treatment of cystic fibrosis caused by nonsense mutations: a prospective phase II trial. *Lancet* 2008; 372:719-27
3. Finkel R S. Read-through strategies for suppression of nonsense mutations in Duchenne/Becker muscular dystrophy: aminoglycosides and ataluren (PTC124). *J Child Neurol* 2010; 25:1158-64
4. Rebbapragada I, Lykke-Andersen J. Execution of nonsense-mediated mRNA decay: what defines a substrate? *Curr Opin Cell Biol* 2009; 21:394-402
5. Linde L, Boelz S, Nissim-Rafinia M, Oren Y S, Wilschanski M, Yaacov Y, Virgilis D, Neu-Yilik G, Kulozik A E, Kerem E, Kerem B. Nonsense-mediated mRNA decay affects nonsense transcript levels and governs response of cystic fibrosis patients to gentamicin. *J Clin Invest* 2007; 117:683-92
6. Linde L, Kerem B. Introducing sense into nonsense in treatments of human genetic diseases. *Trends Genet* 2008; 24:552-63
7. Hua Y, Vickers T A, Baker B F, Bennett C F, Krainer A R. Enhancement of SMN2 exon 7 inclusion by antisense oligonucleotides targeting the exon. *PLoS Biol* 2007; 5:e73
8. Hua Y, Vickers T A, Okunola H L, Bennett C F, Krainer A R. Antisense masking of an hnRNP A1/A2 intronic splicing silencer corrects SMN2 splicing in transgenic mice. *Am J Hum Genet* 2008; 82:834-48
9. Hua Y, Sahashi K, Hung G, Rigo F, Passini M A, Bennett C F, Krainer A R. Antisense correction of SMN2 splicing in the CNS rescues necrosis in a type III SMA mouse model. *Genes Dev* 2010; 24:1634-44
10. Hua Y, Sahashi K, Rigo F, Hung G, Horev G, Bennett C F, Krainer A R. Peripheral SMN restoration is essential for long-term rescue of a severe spinal muscular atrophy mouse model. *Nature* 2011; 478:123-6
11. Le Hir H, Séraphin B. EJCs at the heart of translational control. *Cell* 2008; 133:213-6
13. Hwang J, Maquat L E. Nonsense-mediated mRNA decay (NMD) in animal embryogenesis: to die or not to die, that is the question. *Curr Opin Genet Dev* 2011; 21:422-30
14. Linde L, Boelz S, Neu-Yilik G, Kulozik A E, Kerem B. The efficiency of nonsense-mediated mRNA decay is an inherent character and varies among different cells. *Eur J Hum Genet* 2007; 15:1156-62
15. Keeling K M, Wang D, Dai Y, Murugesan S, Chenna B, Clark J, Belakhov V, Kandasamy J, Velu S E, Baasov T, Bedwell D M. Attenuation of nonsense-mediated mRNA decay enhances in vivo nonsense suppression. *PLoS One*. 2013 Apr. 10; 8(4):e60478
16. Keeling and Bedwell. Suppression of nonsense mutations as a therapeutic approach to treat genetic diseases. *Wiley Interdiscip Rev RNA*. 2011; 2(6):837-52
17. Gong Q, Stump M R, Zhou Z. J. Inhibition of nonsense-mediated mRNA decay by antisense morpholino oligonucleotides restores functional expression of hERG nonsense and frameshift mutations in long-QT syndrome. *Mol Cell Cardiol* 2011; 50:223-9
18. Pichavant C, Aartsma-Rus A, Clemens P R, Davies K E, Dickson G, Takeda S, Wilton S D, Wolff J A, Wooddell C I, Xiao X, Tremblay J P. Current status of pharmaceutical and genetic therapeutic approaches to treat DMD. *Mol Ther* 2011; 19:830-40
19. Sermet-Gaudelus I, Boeck K D, Casimir G J, Vermeulen F, Leal T, Mogenet A, Roussel D, Fritsch J, Hanssens L, Hirawat S, Miller N L, Constantine S, Reha A, Ajayi T, Elfring G L, Miller L L. Ataluren (PTC124) induces cystic fibrosis transmembrane conductance regulator protein expression and activity in children with nonsense mutation cystic fibrosis. *Am J Respir Crit Care Med* 2010; 182:1262-72
20. Salvatori F, Breveglieri G, Zuccato C, Finotti A, Bianchi N, Borgatti M, Feriotto G, Destro F, Canella A, Brognara E, Lampronti I, Breda L, Rivella S, Gambari R. Production of beta-globin and adult hemoglobin following G418 treatment of erythroid precursor cells from homozygous beta(0)39 thalassemia patients. *Am J Hematol.* 2009; 84:720-8
21. Kole R, Krainer A R, Altman S. RNA therapeutics: beyond RNA interference and antisense oligonucleotides. *Nat Rev Drug Discov* 2012; 11:125-40
22. Vecsler M, Ben Zeev B, Nudelman I, Anikster Y, Simon A J, Amariglio N, Rechavi G, Baasov T, Gak E. Ex vivo treatment with a novel synthetic aminoglycoside NB54 in primary fibroblasts from Rett syndrome patients suppresses MECP2 nonsense mutations. *PLoS One* 2011; 6:e20733
23. Le Hir H, Izaurralde E, Maquat L E, Moore M J. The spliceosome deposits multiple proteins from about 20 to about 24 nucleotides upstream of mRNA exon-exon junctions. *EMBO J* 2000; 19:6860-9
24. Singh G, Kucukural A, Cenik C, Leszyk J D, Shaffer S A, Weng Z, Moore M J. The cellular EJC interactome reveals higher-order mRNP structure and an EJC-SR protein nexus. Cell. 2012 Nov. 9; 151(4):750-64
25. Saulière J, Murigneux V, Wang Z, Marquenet E, Barbosa I, Le Tonquèze O, Audic Y, Paillard L, Roest Crollius H, Le Hir H. CLIP-seq of eIF4AIII reveals transcriptome-wide mapping of the human exon junction complex. Nat Struct Mol Biol. 2012 November; 19(11):1124-31
26. Le Hir H, Gatfield D, Izaurralde E, Moore M J. The exon-exon junction complex provides a binding platform for factors involved in mRNA export and nonsense-mediated mRNA decay. EMBO J 2001; 20:4987-97
27. Keene J D, Komisarow J M, Friedersdorf M B. RIP-Chip: the isolation and identification of mRNAs, microRNAs and protein components of ribonucleoprotein complexes from cell extracts. *Nat Protoc* 2006; 1:302-7
28. Yeo G W, Coufal N G, Liang T Y, Peng G E, Fu X D, Gage F H. An RNA code for the FOX2 splicing regulator revealed by mapping RNA-protein interactions in stem cells. *Nat Struct Mol Biol* 2009; 16:130-7
29. Ule J, Jensen K B, Ruggiu M, Mele A, Ule A, Darnell R B. CLIP identifies Nova-regulated RNA networks in the brain. *Science* 2003; 302:1212-5
30. Cristea I M, Williams R, Chait B T, Rout M P. Fluorescent proteins as proteomic probes. *Mol Cell* Proteomics 2005; 4:1933-41
31. Timney B L, Tetenbaum-Novatt J, Agate D S, Williams R, Zhang W, Chait B T, Rout M P. Simple kinetic relationships and nonspecific competition govern nuclear import rates in vivo. *J Cell Biol* 2006; 175:579-93
32. Sugiyama Y, Kawabata I, Sobue K, Okabe S. Determination of absolute protein numbers in single synapses by a GFP-based calibration technique. *Nat Methods* 2005; 2:677-84

EQUIVALENTS AND SCOPE

Those skilled in the art will recognize or be able to ascertain using no more than routine experimentation many equivalents to the specific embodiments described herein. The scope of the present invention is not intended to be limited to the above Description, but rather is as set forth in the appended claims.

Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should be understood that, in general, where the invention, or aspects of the invention, is/are referred to as comprising particular elements, features, certain embodiments of the invention or aspects of the invention consist, or consist essentially of, such elements, features.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

All references cited herein, including patents, published patent applications, and publications, are incorporated by reference in their entirety.

What is claimed is:

1. An antisense oligonucleotide (ASO) that is complementary to a region of mRNA that is transcribed in eukaryotic cells and contains a disease-causing premature termination codon (PTC) derived from a CFTR gene containing a nonsense mutation, wherein the exon-exon junction is located downstream of the PTC, the disease is cystic fibrosis and the region is from about 1 to about 50 nucleotides upstream of the exon-exon junction.

2. An antisense oligonucleotide (ASO) specific to a region of mRNA that is transcribed in a eukaryotic cell, wherein the region of the mRNA is from about 20 to about 24 nucleotides upstream of an exon-exon junction (from about −20 to about −24 nucleotides) that is downstream of a disease-causing premature termination codon (PTC) in the mRNA, wherein the disease is cystic fibrosis and the PTC is derived from a CFTR gene that contains codon change TGGa-TGA, which results in nonsense mutation TRP-Ter and to which deposition of exon junction complexes (EJC) marks the mRNA for nonsense-mediated decay, wherein the ASO is at least 14 nucleotides.

3. An antisense oligonucleotide (ASO) that is complementary to a region of an mRNA that is transcribed in eukaryotic cells and contains a disease-causing premature termination codon (PTC) derived from a CFTR gene containing a nonsense mutation and an exon-exon junction located downstream from the PTC, wherein the disease is cystic fibrosis and the region is from about 1 to about 50 nucleotides upstream of the exon-exon junction, wherein the CFTR gene containing a nonsense mutation is CM900061.

4. The ASO of claim 1, wherein the ASO comprises SEQ ID NO: 107, SEQ ID NO: 83 or SEQ ID NO: 65.

5. The ASO of claim 3, wherein the ASO comprises SEQ ID NO: 107, SEQ ID NO: 83 or SEQ ID NO: 65.

6. The ASO of claim 5, wherein the region of the mRNA is from about 20 to about 24 nucleotides upstream of the exon-exon junction (from about 20 to about 24 nucleotides).

7. The ASO of claim 5, wherein the region of the mRNA is an Exon Junction Complex-protected area or a region adjacent to an Exon-Junction Complex-protected area.

8. The ASO of claim 4 which is at least 95% complementary to the region of the mRNA.

9. The ASO of claim 4 which is from 14 nucleotides to 20 nucleotides.

10. The ASO of claim 2, wherein the ASO hybridizes and remains bound to the region under physiological conditions.

11. The ASO of claim 2, wherein the allele is a CFTR allele and the ASO comprises SEQ ID NO: 107, SEQ ID NO: 83 or SEQ ID NO: 65.

12. An antisense oligonucleotide (ASO) of claim 1, wherein the mRNA is expressed from a CFTR gene that contains the codon change TGGa-TGA at codon 1282 and the amino acid change is Trp-Ter.

13. An antisense oligonucleotide (ASO) that is complementary to a region of an mRNA that (a) is transcribed in eukaryotic cells and (b) contains (1) a disease-causing premature termination codon (PTC) derived from a CFTR gene that contains a nonsense mutation or a naturally-occurring premature termination codon (PTC) and (2) an exon-exon junction located downstream from the PTC, wherein the disease is cystic fibrosis and the region is from about 1 to about 50 nucleotides upstream of the exon-exon junction.

14. An antisense oligonucleotide (ASO) of claim 13, wherein the region of the mRNA is 1 to 49 nucleotides upstream of the exon-exon junction.

15. An antisense oligonucleotide (ASO) of claim 14, wherein the region of the mRNA is 1 to 40 nucleotides upstream of the exon-exon junction.

* * * * *

UNITED STATES PATENT AND TRADEMARK OFFICE
CERTIFICATE OF CORRECTION

PATENT NO. : 10,647,983 B2
APPLICATION NO. : 14/916561
DATED : May 12, 2020
INVENTOR(S) : Adrian Krainer et al.

Page 1 of 1

It is certified that error appears in the above-identified patent and that said Letters Patent is hereby corrected as shown below:

In the Claims

Column 132, Claims 8 and 9 should read:

8. The ASO of claim 6 which is at least 95% complementary to the region of the mRNA.

9. The ASO of claim 6 which is from 14 nucleotides to 20 nucleotides.

Signed and Sealed this
Twentieth Day of October, 2020

Andrei Iancu
*Director of the United States Patent and Trademark Office*

SEQUENCE LISTING

<160> NUMBER OF SEQ ID NOS: 268

<210> SEQ ID NO 1
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 1
gcagcttgtc acagt                                                15

```
<210> SEQ ID NO 2
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 2
tgcagcttgt cacag                                                    15

<210> SEQ ID NO 3
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 3
gtgcagcttg tcaca                                                    15

<210> SEQ ID NO 4
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 4
cgtgcagctt gtcac                                                    15

<210> SEQ ID NO 5
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 5
acgtgcagct tgtca                                                    15

<210> SEQ ID NO 6
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 6
cacgtgcagc ttgtc                                                    15

<210> SEQ ID NO 7
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 7
ccacgtgcag cttgt                                                    15

<210> SEQ ID NO 8
<211> LENGTH: 15
<212> TYPE: DNA
<213> ORGANISM: Artificial Sequence
<220> FEATURE:
<223> OTHER INFORMATION: Synthetic Oligonucleotide
```

<400> SEQUENCE: 8
tccacgtgca gcttg					15

<210> SEQ ID NO 9
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 9
atccacgtgc agctt					15

<210> SEQ ID NO 10
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 10
gatccacgtg cagct					15

<210> SEQ ID NO 11
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 11
ggatccacgt gcagc					15

<210> SEQ ID NO 12
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 12
aggatccacg tgcag					15

<210> SEQ ID NO 13
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 13
caggatccac gtgca					15

<210> SEQ ID NO 14
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 14
tcaggatcca cgtgc					15

<210> SEQ ID NO 15
<211> LENGTH: 15

```
<212> TYPE: DNA
<213> ORGANISM: Artificial Sequence
<220> FEATURE:
<223> OTHER INFORMATION: Synthetic Oligonucleotide

<400> SEQUENCE: 15
ctcaggatcc acgtg                                                    15

<210> SEQ ID NO 16
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 16
tctcaggatc cacgt                                                    15

<210> SEQ ID NO 17
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 17
ttctcaggat ccacg                                                    15

<210> SEQ ID NO 18
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 18
gttctcagga tccac                                                    15

<210> SEQ ID NO 19
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 19
agttctcagg atcca                                                    15

<210> SEQ ID NO 20
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 20
cccagcagag cggcc                                                    15

<210> SEQ ID NO 21
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 21
```

-continued

```
tcccagcaga gcggc                                                15

<210> SEQ ID NO 22
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 22
ttcccagcag agcgg                                                15

<210> SEQ ID NO 23
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 23
cttcccagca gagcg                                                15

<210> SEQ ID NO 24
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 24
acttcccagc agagc                                                15

<210> SEQ ID NO 25
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 25
tacttcccag cagag                                                15

<210> SEQ ID NO 26
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 26
atacttccca gcaga                                                15

<210> SEQ ID NO 27
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 27
catacttccc agcag                                                15

<210> SEQ ID NO 28
<211> LENGTH: 15
<212> TYPE: DNA
<213> ORGANISM: Artificial Sequence
```

```
<220> FEATURE:
<223> OTHER INFORMATION: Synthetic Oligonucleotide

<400> SEQUENCE: 28
tcatacttcc cagca                                                    15

<210> SEQ ID NO 29
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 29
atcatacttc ccagc                                                    15

<210> SEQ ID NO 30
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 30
catcatactt cccag                                                    15

<210> SEQ ID NO 31
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 31
acatcatact tccca                                                    15

<210> SEQ ID NO 32
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 32
cacatcatac ttccc                                                    15

<210> SEQ ID NO 33
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 33
acacatcata cttcc                                                    15

<210> SEQ ID NO 34
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 34
tacacatcat acttc                                                    15
```

```
<210> SEQ ID NO 35
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 35
atacacatca tactt                                                    15

<210> SEQ ID NO 36
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 36
aatacacatc atact                                                    15

<210> SEQ ID NO 37
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 37
aaatacacat catac                                                    15

<210> SEQ ID NO 38
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 38
caaatacaca tcata                                                    15

<210> SEQ ID NO 39
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 39
tcctccactg ttgca                                                    15

<210> SEQ ID NO 40
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 40
ttcctccact gttgc                                                    15

<210> SEQ ID NO 41
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 41
tttcctccac tgttg                                                    15

<210> SEQ ID NO 42
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 42
ctttcctcca ctgtt                                                    15

<210> SEQ ID NO 43
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 43
gctttcctcc actgt                                                    15

<210> SEQ ID NO 44
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 44
ggctttcctc cactg                                                    15

<210> SEQ ID NO 45
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 45
aggctttcct ccact                                                    15

<210> SEQ ID NO 46
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 46
aaggctttcc tccac                                                    15

<210> SEQ ID NO 47
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 47
aaaggctttc ctcca                                                    15

<210> SEQ ID NO 48
```

```
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 48
caaaggcttt cctcc                                                      15

<210> SEQ ID NO 49
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 49
ccaaaggctt tcctc                                                      15

<210> SEQ ID NO 50
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 50
tccaaaggct ttcct                                                      15

<210> SEQ ID NO 51
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 51
ctccaaaggc tttcc                                                      15

<210> SEQ ID NO 52
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 52
actccaaagg ctttc                                                      15

<210> SEQ ID NO 53
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 53
cactccaaag gcttt                                                      15

<210> SEQ ID NO 54
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 54
```
tcactccaaa ggctt                                                        15

<210> SEQ ID NO 55
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 55
atcactccaa aggct                                                        15

<210> SEQ ID NO 56
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 56
tatcactcca aggc                                                         15

<210> SEQ ID NO 57
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 57
gtatcactcc aaagg                                                        15

<210> SEQ ID NO 58
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 58
cttgatcact ccact                                                        15

<210> SEQ ID NO 59
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 59
tcttgatcac tccac                                                        15

<210> SEQ ID NO 60
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 60
ttcttgatca ctcca                                                        15

<210> SEQ ID NO 61
<211> LENGTH: 15
<212> TYPE: DNA

<213> ORGANISM: Artificial Sequence
<220> FEATURE:
<223> OTHER INFORMATION: Synthetic Oligonucleotide

<400> SEQUENCE: 61
tttcttgatc actcc                                                    15

<210> SEQ ID NO 62
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 62
atttcttgat cactc                                                    15

<210> SEQ ID NO 63
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 63
tatttcttga tcact                                                    15

<210> SEQ ID NO 64
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 64
atatttcttg atcac                                                    15

<210> SEQ ID NO 65
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 65
catatttctt gatca                                                    15

<210> SEQ ID NO 66
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 66
ccatatttct tgatc                                                    15

<210> SEQ ID NO 67
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 67
tccatatttc ttgat                                                    15

<210> SEQ ID NO 68
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 68
ttccatattt cttga                                                    15

<210> SEQ ID NO 69
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 69
tttccatatt tcttg                                                    15

<210> SEQ ID NO 70
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 70
ctttccatat ttctt                                                    15

<210> SEQ ID NO 71
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 71
actttccata tttct                                                    15

<210> SEQ ID NO 72
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 72
aactttccat atttc                                                    15

<210> SEQ ID NO 73
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 73
caactttcca tattt                                                    15

<210> SEQ ID NO 74
<211> LENGTH: 15
<212> TYPE: DNA
<213> ORGANISM: Artificial Sequence
<220> FEATURE:

```
<223> OTHER INFORMATION: Synthetic Oligonucleotide

<400> SEQUENCE: 74
gcaactttcc atatt                                                        15

<210> SEQ ID NO 75
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 75
tgcaactttc catat                                                        15

<210> SEQ ID NO 76
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 76
ctgcaacttt ccata                                                        15

<210> SEQ ID NO 77
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 77
ttcatcaagc agcaa                                                        15

<210> SEQ ID NO 78
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 78
gttcatcaag cagca                                                        15

<210> SEQ ID NO 79
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 79
ggttcatcaa gcagc                                                        15

<210> SEQ ID NO 80
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 80
gggttcatca agcag                                                        15
```

```
<210> SEQ ID NO 81
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 81
tgggttcatc aagca                                                    15

<210> SEQ ID NO 82
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 82
ctgggttcat caagc                                                    15

<210> SEQ ID NO 83
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 83
actgggttca tcaag                                                    15

<210> SEQ ID NO 84
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 84
cactgggttc atcaa                                                    15

<210> SEQ ID NO 85
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 85
gcactgggtt catca                                                    15

<210> SEQ ID NO 86
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 86
agcactgggt tcatc                                                    15

<210> SEQ ID NO 87
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 87
gagcactggg ttcat                                                      15

<210> SEQ ID NO 88
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 88
tgagcactgg gttca                                                      15

<210> SEQ ID NO 89
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 89
atgagcactg ggttc                                                      15

<210> SEQ ID NO 90
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 90
aatgagcact gggtt                                                      15

<210> SEQ ID NO 91
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 91
aaatgagcac tgggt                                                      15

<210> SEQ ID NO 92
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 92
caaatgagca ctggg                                                      15

<210> SEQ ID NO 93
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 93
ccaaatgagc actgg                                                      15

<210> SEQ ID NO 94
<211> LENGTH: 15
```

<212> TYPE: DNA
<213> ORGANISM: Artificial Sequence
<220> FEATURE:
<223> OTHER INFORMATION: Synthetic Oligonucleotide

<400> SEQUENCE: 94
tccaaatgag cactg                                                      15

<210> SEQ ID NO 95
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 95
atccaaatga gcact                                                      15

<210> SEQ ID NO 96
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 96
ttgcttctat cctgt                                                      15

<210> SEQ ID NO 97
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 97
attgcttcta tcctg                                                      15

<210> SEQ ID NO 98
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 98
cattgcttct atcct                                                      15

<210> SEQ ID NO 99
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 99
gcattgcttc tatcc                                                      15

<210> SEQ ID NO 100
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 100
agcattgctt ctatc                                                    15

<210> SEQ ID NO 101
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 101
cagcattgct tctat                                                    15

<210> SEQ ID NO 102
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 102
ccagcattgc ttcta                                                    15

<210> SEQ ID NO 103
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 103
tccagcattg cttct                                                    15

<210> SEQ ID NO 104
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 104
ttccagcatt gcttc                                                    15

<210> SEQ ID NO 105
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 105
attccagcat tgctt                                                    15

<210> SEQ ID NO 106
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 106
cattccagca ttgct                                                    15

<210> SEQ ID NO 107
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 107
gcattccagc attgc                                                  15

<210> SEQ ID NO 108
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 108
ggcattccag cattg                                                  15

<210> SEQ ID NO 109
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 109
tggcattcca gcatt                                                  15

<210> SEQ ID NO 110
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 110
ttggcattcc agcat                                                  15

<210> SEQ ID NO 111
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 111
gttggcattc cagca                                                  15

<210> SEQ ID NO 112
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 112
tgttggcatt ccagc                                                  15

<210> SEQ ID NO 113
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 113
ttgttggcat tccag                                                  15

<210> SEQ ID NO 114
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 114
attgttggca ttcca                                                        15

<210> SEQ ID NO 115
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 115
taggattctc tctag                                                        15

<210> SEQ ID NO 116
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 116
ctaggattct ctcta                                                        15

<210> SEQ ID NO 117
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 117
gctaggattc tctct                                                        15

<210> SEQ ID NO 118
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 118
tgctaggatt ctctc                                                        15

<210> SEQ ID NO 119
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 119
ctgctaggat tctct                                                        15

<210> SEQ ID NO 120
<211> LENGTH: 15
<212> TYPE: DNA
<213> ORGANISM: Artificial Sequence
<220> FEATURE:
<223> OTHER INFORMATION: Synthetic Oligonucleotide

```
<400> SEQUENCE: 120
tctgctagga ttctc                                                      15

<210> SEQ ID NO 121
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 121
atctgctagg attct                                                      15

<210> SEQ ID NO 122
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 122
gatctgctag gattc                                                      15

<210> SEQ ID NO 123
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 123
agatctgcta ggatt                                                      15

<210> SEQ ID NO 124
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 124
aagatctgct aggat                                                      15

<210> SEQ ID NO 125
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 125
caagatctgc tagga                                                      15

<210> SEQ ID NO 126
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 126
tcaagatctg ctagg                                                      15

<210> SEQ ID NO 127
```

```
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 127
ctcaagatct gctag                                                          15

<210> SEQ ID NO 128
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 128
cctcaagatc tgcta                                                          15

<210> SEQ ID NO 129
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 129
tcctcaagat ctgct                                                          15

<210> SEQ ID NO 130
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 130
ttcctcaaga tctgc                                                          15

<210> SEQ ID NO 131
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 131
cttcctcaag atctg                                                          15

<210> SEQ ID NO 132
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 132
tcttcctcaa gatct                                                          15

<210> SEQ ID NO 133
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 133
```
ttcttcctca agatc                                                    15

<210> SEQ ID NO 134
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 134
tgtgtaactg tgact                                                    15

<210> SEQ ID NO 135
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 135
ctgtgtaact gtgac                                                    15

<210> SEQ ID NO 136
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 136
cctgtgtaac tgtga                                                    15

<210> SEQ ID NO 137
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 137
gcctgtgtaa ctgtg                                                    15

<210> SEQ ID NO 138
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 138
agcctgtgta actgt                                                    15

<210> SEQ ID NO 139
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 139
tagcctgtgt aactg                                                    15

<210> SEQ ID NO 140
<211> LENGTH: 15
<212> TYPE: DNA

```
<213> ORGANISM: Artificial Sequence
<220> FEATURE:
<223> OTHER INFORMATION: Synthetic Oligonucleotide

<400> SEQUENCE: 140
ttagcctgtg taact                                                  15

<210> SEQ ID NO 141
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 141
cttagcctgt gtaac                                                  15

<210> SEQ ID NO 142
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 142
ccttagcctg tgtaa                                                  15

<210> SEQ ID NO 143
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 143
gccttagcct gtgta                                                  15

<210> SEQ ID NO 144
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 144
tgccttagcc tgtgt                                                  15

<210> SEQ ID NO 145
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 145
ctgccttagc ctgtg                                                  15

<210> SEQ ID NO 146
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 146
gctgccttag cctgt                                                  15
```

<210> SEQ ID NO 147
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 147
agctgcctta gcctg                                                        15

<210> SEQ ID NO 148
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 148
cagctgcctt agcct                                                        15

<210> SEQ ID NO 149
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 149
gcagctgcct tagcc                                                        15

<210> SEQ ID NO 150
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 150
agcagctgcc ttagc                                                        15

<210> SEQ ID NO 151
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 151
cagcagctgc cttag                                                        15

<210> SEQ ID NO 152
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 152
ccagcagctg cctta                                                        15

<210> SEQ ID NO 153
<211> LENGTH: 15
<212> TYPE: DNA
<213> ORGANISM: Artificial Sequence
<220> FEATURE:

<223> OTHER INFORMATION: Synthetic Oligonucleotide

<400> SEQUENCE: 153
ccaaccactc ggagc                                                     15

<210> SEQ ID NO 154
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 154
gccaaccact cggag                                                     15

<210> SEQ ID NO 155
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 155
tgccaaccac tcgga                                                     15

<210> SEQ ID NO 156
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 156
ctgccaacca ctcgg                                                     15

<210> SEQ ID NO 157
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 157
actgccaacc actcg                                                     15

<210> SEQ ID NO 158
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 158
gactgccaac cactc                                                     15

<210> SEQ ID NO 159
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 159
tgactgccaa ccact                                                     15

```
<210> SEQ ID NO 160
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 160
ttgactgcca accac                                                      15

<210> SEQ ID NO 161
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 161
tttgactgcc aacca                                                      15

<210> SEQ ID NO 162
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 162
gtttgactgc caacc                                                      15

<210> SEQ ID NO 163
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 163
agtttgactg ccaac                                                      15

<210> SEQ ID NO 164
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 164
aagtttgact gccaa                                                      15

<210> SEQ ID NO 165
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 165
gaagtttgac tgcca                                                      15

<210> SEQ ID NO 166
<211> LENGTH: 15
<212> TYPE: DNA
<213> ORGANISM: Artificial Sequence
<220> FEATURE:
<223> OTHER INFORMATION: Synthetic Oligonucleotide
```

<400> SEQUENCE: 166
cgaagtttga ctgcc                                                    15

<210> SEQ ID NO 167
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 167
ccgaagtttg actgc                                                    15

<210> SEQ ID NO 168
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 168
tccgaagttt gactg                                                    15

<210> SEQ ID NO 169
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 169
gtccgaagtt tgact                                                    15

<210> SEQ ID NO 170
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 170
agtccgaagt ttgac                                                    15

<210> SEQ ID NO 171
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 171
gagtccgaag tttga                                                    15

<210> SEQ ID NO 172
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 172
ttgagttgct ccatc                                                    15

<210> SEQ ID NO 173
<211> LENGTH: 15

```
<212> TYPE: DNA
<213> ORGANISM: Artificial Sequence
<220> FEATURE:
<223> OTHER INFORMATION: Synthetic Oligonucleotide

<400> SEQUENCE: 173
gttgagttgc tccat                                                    15

<210> SEQ ID NO 174
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 174
tgttgagttg ctcca                                                    15

<210> SEQ ID NO 175
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 175
ttgttgagtt gctcc                                                    15

<210> SEQ ID NO 176
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 176
gttgttgagt tgctc                                                    15

<210> SEQ ID NO 177
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 177
agttgttgag ttgct                                                    15

<210> SEQ ID NO 178
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 178
gagttgttga gttgc                                                    15

<210> SEQ ID NO 179
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 179
```
ggagttgttg agttg 15

<210> SEQ ID NO 180
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 180
aggagttgtt gagtt 15

<210> SEQ ID NO 181
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 181
aaggagttgt tgagt 15

<210> SEQ ID NO 182
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 182
gaaggagttg ttgag 15

<210> SEQ ID NO 183
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 183
ggaaggagtt gttga 15

<210> SEQ ID NO 184
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 184
gggaaggagt tgttg 15

<210> SEQ ID NO 185
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 185
agggaaggag ttgtt 15

<210> SEQ ID NO 186
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 186
tagggaagga gttgt                                                    15

<210> SEQ ID NO 187
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 187
ctagggaagg agttg                                                    15

<210> SEQ ID NO 188
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 188
actagggaag gagtt                                                    15

<210> SEQ ID NO 189
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 189
aactagggaa ggagt                                                    15

<210> SEQ ID NO 190
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 190
gaactaggga aggag                                                    15

<210> SEQ ID NO 191
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 191
agccgcaggg tcacc                                                    15

<210> SEQ ID NO 192
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 192
cagccgcagg gtcac                                                    15

<210> SEQ ID NO 193
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 193
gcagccgcag ggtca                                                    15

<210> SEQ ID NO 194
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 194
cgcagccgca gggtc                                                    15

<210> SEQ ID NO 195
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 195
gcgcagccgc agggt                                                    15

<210> SEQ ID NO 196
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 196
cgcgcagccg caggg                                                    15

<210> SEQ ID NO 197
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 197
ccgcgcagcc gcagg                                                    15

<210> SEQ ID NO 198
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 198
cccgcgcagc cgcag                                                    15

<210> SEQ ID NO 199
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 199
ccccgcgcag ccgca                                                                 15

<210> SEQ ID NO 200
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 200
accccgcgca gccgc                                                                 15

<210> SEQ ID NO 201
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 201
caccccgcgc agccg                                                                 15

<210> SEQ ID NO 202
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 202
gcaccccgcg cagcc                                                                 15

<210> SEQ ID NO 203
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 203
ggcaccccgc gcagc                                                                 15

<210> SEQ ID NO 204
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 204
gggcaccccg cgcag                                                                 15

<210> SEQ ID NO 205
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 205
actgctctgc cgtgg                                                                 15

<210> SEQ ID NO 206

```
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 206
aactgctctg ccgtg                                                      15

<210> SEQ ID NO 207
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 207
gaactgctct gccgt                                                      15

<210> SEQ ID NO 208
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 208
ggaactgctc tgccg                                                      15

<210> SEQ ID NO 209
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 209
cggaactgct ctgcc                                                      15

<210> SEQ ID NO 210
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 210
ccggaactgc tctgc                                                      15

<210> SEQ ID NO 211
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 211
gccggaactg ctctg                                                      15

<210> SEQ ID NO 212
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 212
```
cgccggaact gctct                                                          15

<210> SEQ ID NO 213
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 213
gcgccggaac tgctc                                                          15

<210> SEQ ID NO 214
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 214
tgcgccggaa ctgct                                                          15

<210> SEQ ID NO 215
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 215
atgcgccgga actgc                                                          15

<210> SEQ ID NO 216
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 216
catgcgccgg aactg                                                          15

<210> SEQ ID NO 217
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 217
gcatgcgccg gaact                                                          15

<210> SEQ ID NO 218
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 218
cgcatgcgcc ggaac                                                          15

<210> SEQ ID NO 219
<211> LENGTH: 15
<212> TYPE: DNA

```
<213> ORGANISM: Artificial Sequence
<220> FEATURE:
<223> OTHER INFORMATION: Synthetic Oligonucleotide

<400> SEQUENCE: 219
gcgcatgcgc cggaa                                                    15

<210> SEQ ID NO 220
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 220
cgcgcatgcg ccgga                                                    15

<210> SEQ ID NO 221
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 221
gcgcgcatgc gccgg                                                    15

<210> SEQ ID NO 222
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 222
cgcgcgcatg cgccg                                                    15

<210> SEQ ID NO 223
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 223
ccgcgcgcat gcgcc                                                    15

<210> SEQ ID NO 224
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 224
gcgcacacac gtgca                                                    15

<210> SEQ ID NO 225
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 225
cgcgcacaca cgtgc                                                    15
```

```
<210> SEQ ID NO 226
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 226
gcgcgcacac acgtg                                                    15

<210> SEQ ID NO 227
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 227
ggcgcgcaca cacgt                                                    15

<210> SEQ ID NO 228
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 228
gggcgcgcac acacg                                                    15

<210> SEQ ID NO 229
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 229
gggcggcttc tcggg                                                    15

<210> SEQ ID NO 230
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 230
cgggcggctt ctcgg                                                    15

<210> SEQ ID NO 231
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 231
ccagaccaga accag                                                    15

<210> SEQ ID NO 232
<211> LENGTH: 15
<212> TYPE: DNA
<213> ORGANISM: Artificial Sequence
<220> FEATURE:
```

```
<223> OTHER INFORMATION: Synthetic Oligonucleotide

<400> SEQUENCE: 232
accagaccag aacca                                                    15

<210> SEQ ID NO 233
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 233
gaccagacca gaacc                                                    15

<210> SEQ ID NO 234
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 234
cgaccagacc agaac                                                    15

<210> SEQ ID NO 235
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 235
ccgaccagac cagaa                                                    15

<210> SEQ ID NO 236
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 236
tccgaccaga ccaga                                                    15

<210> SEQ ID NO 237
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 237
atccgaccag accag                                                    15

<210> SEQ ID NO 238
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 238
catccgacca gacca                                                    15
```

```
<210> SEQ ID NO 239
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 239
tcatccgacc agacc                                                        15

<210> SEQ ID NO 240
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 240
ttcatccgac cagac                                                        15

<210> SEQ ID NO 241
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 241
gttcatccga ccaga                                                        15

<210> SEQ ID NO 242
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 242
tgttcatccg accag                                                        15

<210> SEQ ID NO 243
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 243
gtgttcatcc gacca                                                        15

<210> SEQ ID NO 244
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 244
cgtgttcatc cgacc                                                        15

<210> SEQ ID NO 245
<211> LENGTH: 15
<212> TYPE: DNA
<213> ORGANISM: Artificial Sequence
<220> FEATURE:
<223> OTHER INFORMATION: Synthetic Oligonucleotide
```

```
<400> SEQUENCE: 245
acgtgttcat ccgac                                                          15

<210> SEQ ID NO 246
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 246
cacgtgttca tccga                                                          15

<210> SEQ ID NO 247
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 247
ccacgtgttc atccg                                                          15

<210> SEQ ID NO 248
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 248
cccacgtgtt catcc                                                          15

<210> SEQ ID NO 249
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 249
gcccacgtgt tcatc                                                          15

<210> SEQ ID NO 250
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 250
aaggtcgatg gcttc                                                          15

<210> SEQ ID NO 251
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 251
gaaggtcgat ggctt                                                          15
```

```
<210> SEQ ID NO 252
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 252
tgaaggtcga tggct                                                    15

<210> SEQ ID NO 253
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 253
ttgaaggtcg atggc                                                    15

<210> SEQ ID NO 254
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 254
gttgaaggtc gatgg                                                    15

<210> SEQ ID NO 255
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 255
ggttgaaggt cgatg                                                    15

<210> SEQ ID NO 256
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 256
aggttgaagg tcgat                                                    15

<210> SEQ ID NO 257
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 257
gaggttgaag gtcga                                                    15

<210> SEQ ID NO 258
<211> LENGTH: 15
<212> TYPE: DNA
<213> ORGANISM: Artificial Sequence
<220> FEATURE:
<223> OTHER INFORMATION: Synthetic Oligonucleotide
```

<400> SEQUENCE: 258
agaggttgaa ggtcg                                                        15

<210> SEQ ID NO 259
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 259
aagaggttga aggtc                                                        15

<210> SEQ ID NO 260
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 260
aaagaggttg aaggt                                                        15

<210> SEQ ID NO 261
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 261
caaagaggtt gaagg                                                        15

<210> SEQ ID NO 262
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 262
acaaagaggt tgaag                                                        15

<210> SEQ ID NO 263
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 263
cacaaagagg ttgaa                                                        15

<210> SEQ ID NO 264
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 264
acacaaagag gttga                                                        15

```
<210> SEQ ID NO 265
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 265
aacacaaaga ggttg                                                    15

<210> SEQ ID NO 266
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 266
gaacacaaag aggtt                                                    15

<210> SEQ ID NO 267
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 267
tgaacacaaa gaggt                                                    15

<210> SEQ ID NO 268
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 268
ctgaacacaa agagg                                                    15
```